(12) United States Patent
Blacklidge et al.

(10) Patent No.: US 12,290,294 B2
(45) Date of Patent: *May 6, 2025

(54) BONE FIXATION ASSEMBLY, IMPLANTS AND METHODS OF USE

(71) Applicant: Paragon 28, Inc., Englewood, CO (US)

(72) Inventors: Douglas K. Blacklidge, Zionsville, IN (US); Laura Zagrocki Brinker, Lone Tree, CO (US); John Mullins, Dublin (IE); Frank Barmes, Parker, CO (US)

(73) Assignee: Paragon 28, Inc., Englewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/363,385

(22) Filed: Aug. 1, 2023

(65) Prior Publication Data
US 2024/0016527 A1 Jan. 18, 2024

Related U.S. Application Data

(63) Continuation of application No. 17/456,731, filed on Nov. 29, 2021, now Pat. No. 11,712,275, which is a
(Continued)

(51) Int. Cl.
*A61B 17/80* (2006.01)
*A61B 17/16* (2006.01)
(Continued)

(52) U.S. Cl.
CPC ...... *A61B 17/8061* (2013.01); *A61B 17/1682* (2013.01); *A61B 17/1775* (2016.11);
(Continued)

(58) Field of Classification Search
CPC ............. A61B 17/8061; A61B 17/8014; A61F 2/4225; A61F 2002/4233; A61F 2002/4238

See application file for complete search history.

(56) References Cited

U.S. PATENT DOCUMENTS 7,740,630 B2   6/2010   Michelson
8,182,484 B2   5/2012   Grant
(Continued)

FOREIGN PATENT DOCUMENTS

WO   2017087957   5/2017

*Primary Examiner* — Tracy L Kamikawa
(74) *Attorney, Agent, or Firm* — Heslin Rothenberg Farley & Mesiti P.C.; Jacquelyn A. Graff, Esq.

(57) ABSTRACT

Bone fusion system, plate system, guide, implant, kit and methods for using the bone fusion system, plate system, guide and implant are disclosed. The bone fusion system includes an alignment guide, an implant, and at least one fastener inserted through the implant. The alignment guide includes a body portion, a first lobe positioned at a first end of the body portion, a second lobe positioned at a second end of the body portion, and an extension member extending away from a first side of the body portion. The implant includes a body portion, a first arm extending away from the body portion in a first direction, a second arm extending away from the body portion in a second direction, and a third arm extending away from the body portion laterally between first and second arms. Finally, methods for using the bone fusion system, plate system, guide and implant are disclosed.

4 Claims, 20 Drawing Sheets

Related U.S. Application Data continuation of application No. 15/836,416, filed on Dec. 8, 2017, now Pat. No. 11,185,356, which is a continuation of application No. PCT/US2017/065315, filed on Dec. 8, 2017.

(51) Int. Cl.
    *A61B 17/17*     (2006.01)
    *A61F 2/42*     (2006.01)
    *A61B 90/00*     (2016.01)

(52) U.S. Cl.
    CPC ........ *A61F 2/4225* (2013.01); *A61B 17/8014* (2013.01); *A61B 2090/0427* (2016.02); *A61B 2090/062* (2016.02); *A61F 2002/4233* (2013.01); *A61F 2002/4238* (2013.01)

(56) References Cited

U.S. PATENT DOCUMENTS

| | | | |
|---|---|---|---|
| 8,197,521 | B2 | 6/2012 | Sixto, Jr. |
| 8,273,111 | B2 * | 9/2012 | Amato ............... A61B 17/8028 606/280 |
| 8,470,003 | B2 | 6/2013 | Voellmicke |
| 8,529,608 | B2 | 9/2013 | Terrill |
| 8,556,946 | B2 | 10/2013 | Prandi |
| 8,685,069 | B2 | 4/2014 | Courtney |
| 9,060,822 | B2 | 6/2015 | Lewis |
| 9,168,075 | B2 | 10/2015 | Dell'Oca |
| 9,254,154 | B2 | 2/2016 | Gonzalez-Hernandez |
| 9,421,103 | B2 | 8/2016 | Jeng |
| 9,795,424 | B2 | 10/2017 | Austin |
| 9,814,505 | B2 | 11/2017 | Leemrijse |
| 11,185,356 | B2 * | 11/2021 | Blacklidge ......... A61B 17/1682 |
| 11,712,275 | B2 * | 8/2023 | Blacklidge ......... A61B 17/8061 606/87 |
| 2004/0210219 | A1 | 10/2004 | Bray |
| 2010/0069966 | A1 | 3/2010 | Castaneda |
| 2010/0222779 | A1 | 9/2010 | Ziemek |
| 2010/0312286 | A1 | 12/2010 | Dell'Oca |
| 2011/0184413 | A1 | 7/2011 | Slater |
| 2011/0295324 | A1 | 12/2011 | Donley |
| 2012/0197261 | A1 | 8/2012 | Rocci |
| 2013/0090695 | A1 | 4/2013 | Bernstein et al. |
| 2013/0150899 | A1 | 6/2013 | Sixto, Jr. et al. |
| 2013/0172942 | A1 | 7/2013 | Lewis et al. |
| 2014/0107798 | A1 | 4/2014 | Jeng et al. |
| 2014/0277176 | A1 | 9/2014 | Buchanan et al. |
| 2015/0045837 | A1 | 2/2015 | Parekh et al. |
| 2015/0335366 | A1 | 11/2015 | Dacosta et al. |
| 2016/0030064 | A1 | 2/2016 | Dacosta et al. |
| 2016/0051297 | A1 | 2/2016 | Steffensmeier et al. |
| 2016/0135858 | A1 * | 5/2016 | Dacosta ............ A61B 17/1728 606/280 |
| 2017/0020537 | A1 | 1/2017 | Tuten |
| 2017/0035479 | A1 | 2/2017 | Paik |
| 2018/0296257 | A1 * | 10/2018 | Penzimer ........... A61B 17/8625 |

* cited by examiner

BONE FIXATION ASSEMBLY, IMPLANTS AND METHODS OF USE

CROSS REFERENCE TO RELATED APPLICATION

This application is a continuation of U.S. application Ser. No. 17/456,731 filed Nov. 29, 2021 and entitled Bone Fixation Assembly, Implants and Methods of Use, which issues as U.S. Pat. No. 11,712,275 on Aug. 1, 2023, which is a continuation of U.S. application Ser. No. 15/836,416 filed Dec. 8, 2017 and entitled Bone Fixation Assembly, Implants and Methods of Use, which issued as U.S. Pat. No. 11,185,356 on Nov. 30, 2021, which is a continuation of PCT Application No. PCT/US2017/065315 filed Dec. 8, 2017 and entitled Bone Fixation Assembly, Implants and Methods of Use, which are incorporated herein by reference in their entireties.

FIELD OF INVENTION

The present disclosure relates generally to general surgery and orthopaedic implants used for achieving bone fusion. More specifically, but not exclusively, the present disclosure relates to surgical devices for fixation of human bones, such as, the foot bones, and to the internal fixation of the proximal portion of metatarsal bones to the bones of the mid-foot and rear-foot to stabilize the realignment of a fracture, dislocation, fusion or the like of the tarso-metatarsal joints, mid-foot and rearfoot.

BACKGROUND OF THE INVENTION

The proximal metatarsal base at its articulation with the mid-tarsus of the human foot is a common site of fracture and/or dislocation especially in persons with neuropathy (neuropathic arthropathy or Charcot joints). The metatarsals at the mid-tarsal articulation displace dorsally and lead to progressive deformity and instability of the foot. Ultimately this can progress to a deformity that leads to excessive soft tissue pressures of the plantar foot and wound development. This type of wound is difficult to heal due to the forces in this area from weight bearing. Instability and deformity of the mid-foot can lead to infection-prone wounds that often result in amputation. Realignment and stabilization of the joints can provide a more anatomic alignment to the foot, provide stability, and dramatically decrease wound and associated amputation risk.

Stable fixation of the metatarsus, mid-tarsus and tarsus can be challenging with currently available devices. A variety of bone screws serving as "beams" have been used in attempt to provide fixation of these foot bone segments. They are most effective at providing stability to the bones of the tarsus and mid-tarsus. The smaller metatarsal bones are particularly difficult to include in "beam" screw fixation. The first metatarsal bone can be fixated by an axial "beam" screw due to its size and alignment with respect to the mid-tarsus and tarsus, however, the smaller metatarsals do not lend themselves to this type of fixation. Alternatively, dorsal plates and screws are used to maintain realignment of the metatarsal bases to the mid-tarsus. Currently available bone fixation plates in this area do not span the metatarsal, mid-tarsal, and tarsal foot segments well without excessive bulk and soft tissue disruption.

The challenge for "beam" screw fixation of the smaller metatarsals is the size of the beam screw needed to prevent screw failure as compared the size of the metatarsal being fixated. Significant violation of the metatarsal base would occur with insertion of a large screw from the proximal metatarsal extending through the mid-tarsus and ending in the tarsus. An ideal "beam" screw construct for stabilization of a relocated metatarsal to mid-tarsal to tarsal foot bone segments would include multiple large diameter screws spanning all three of these bone segments. "Beam" screw fixation inclusive of metatarsal bases 2-5 is suboptimal with current device options.

Accordingly, it is an object of the present disclosure to overcome one or more of the above-described drawbacks and/or disadvantages of the currently used procedures. For example, in view of the deficiencies of the currently available implants and methods of fixing the proximal portion of metatarsal bones (base) to the bones of the mid-foot and rear-foot to stabilize realignment of a fracture, dislocation, fusion or the like of the tarso-metatarsal joints, mid-foot and rear-foot that overcomes the deficiencies of the prior art, it would be desirable to develop devices, systems, instrumentation, and methods for maintaining, correcting and/or fusing joint deformities to overcome the above-noted drawbacks of the currently available implant and surgical solutions.

SUMMARY OF THE INVENTION

Aspects of the present disclosure provide bone fixation devices for use in a method of fusing bones. Specifically, the present disclosure relates to surgical devices and methods for fixation of human bones, such as, the foot bones, and to the internal fixation of the proximal portion of metatarsal bones to the bones of the mid-foot and rear-foot to stabilize realignment of a fracture, dislocation, fusion or the like of the tarso-metatarsal joints, mid-foot and rear-foot.

In one aspect, provided herein is a bone fusion system, including an alignment guide, an implant, and at least one fastener inserted through the implant.

In another aspect, provided herein is an alignment guide, including a body portion, a first lobe positioned at a first end of the body portion, a second lobe positioned at a second end of the body portion, and an extension member extending away from a first side of the body portion.

In yet another aspect, provided herein is an implant, including a body portion, a first arm extending away from the body portion in a first direction, a second arm extending away from the body portion in a second direction, and a third arm extending away from the body portion laterally at a position between the first arm and the second arm.

In a further aspect, provided herein is a method for using a fusion system, including preparing at least one joint and inserting temporary fixation k-wires across the at least one joint. The method may also include obtaining an alignment guide and positioning the alignment guide on a foot over the at least one joint. In addition, the method may include reaming a recess into the at least one joint and positioning an implant on the foot. The implant, includes a body portion, a first arm extending away from the body portion in a first direction, a second arm extending away from the body portion in a second direction, a third arm extending away from the body portion laterally at a position between the first arm and the second arm, and an extension member extending away from a bottom surface of the third arm. The extension member is inserted into the recess in the at least one joint. The method further includes fixing the implant to the foot, removing the temporary fixation k-wires, and closing an incision.

These, and other objects, features and advantages of this disclosure will become apparent from the following detailed description of the various aspects of the disclosure taken in conjunction with the accompanying drawings.

BRIEF DESCRIPTION OF THE DRAWINGS

The accompanying drawings, which are incorporated in and constitute a part of the specification, illustrate embodiments of the disclosure and together with the detailed description herein, serve to explain the principles of the disclosure. The drawings are only for purposes of illustrating preferred embodiments and are not to be construed as limiting the disclosure. It is emphasized that, in accordance with the standard practice in the industry, various features are not drawn to scale. In fact, the dimensions of the various features may be arbitrarily increased or reduced for clarity of discussion. The foregoing and other objects, features and advantages of the disclosure are apparent from the following detailed description taken in conjunction with the accompanying drawings in which.

DETAILED DESCRIPTION OF THE INVENTION

Figure 1:
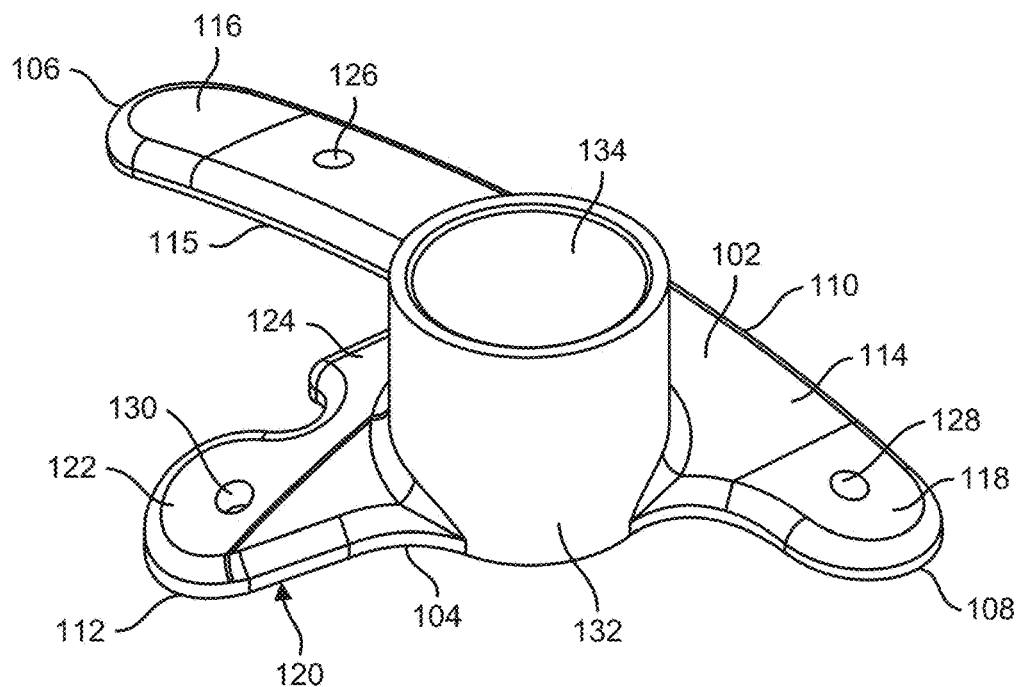
FIG. 1 is a second end, top perspective view of an alignment guide, in accordance with an aspect of the present disclosure.
Figure 2:
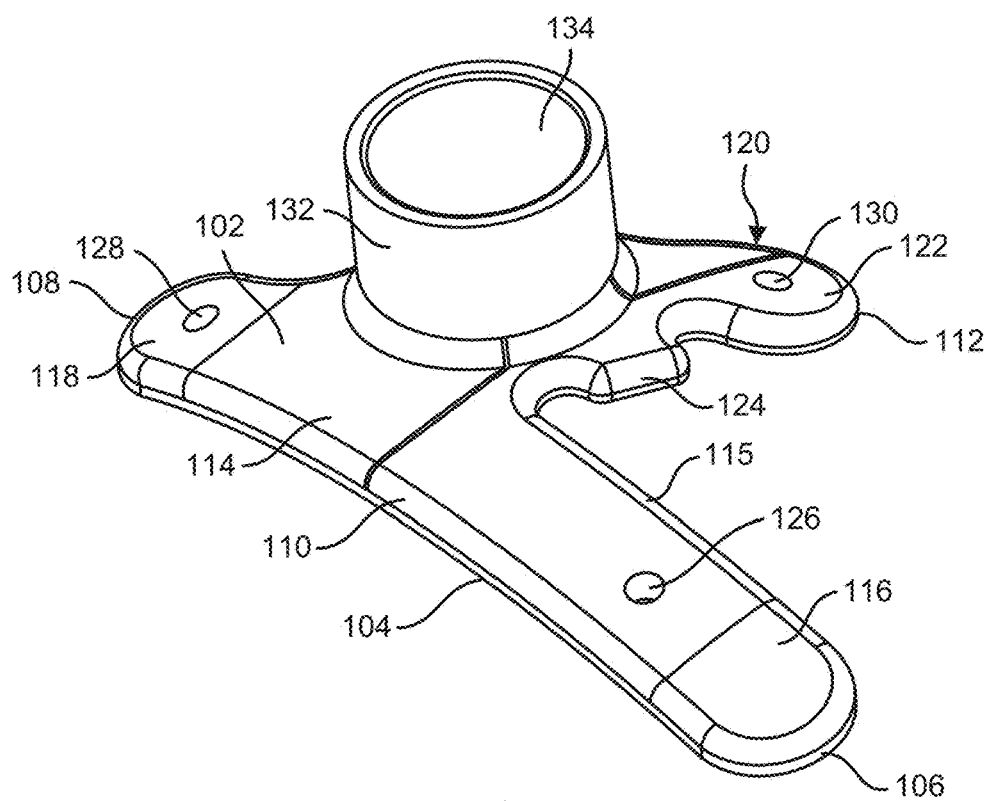
FIG. 2 is a first end, top perspective view of the alignment guide of FIG. 1, in accordance with an aspect of the present disclosure.
Figure 3:
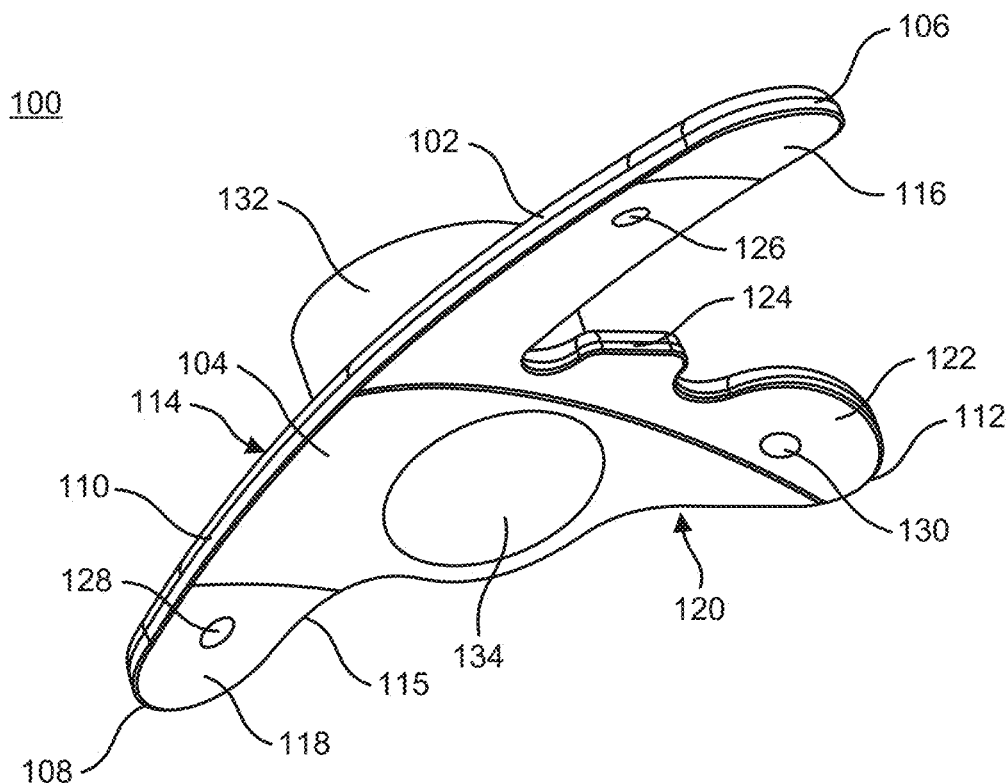
FIG. 3 is a first end, bottom perspective view of the alignment guide of FIG. 1, in accordance with an aspect of the present disclosure.
Figure 4:
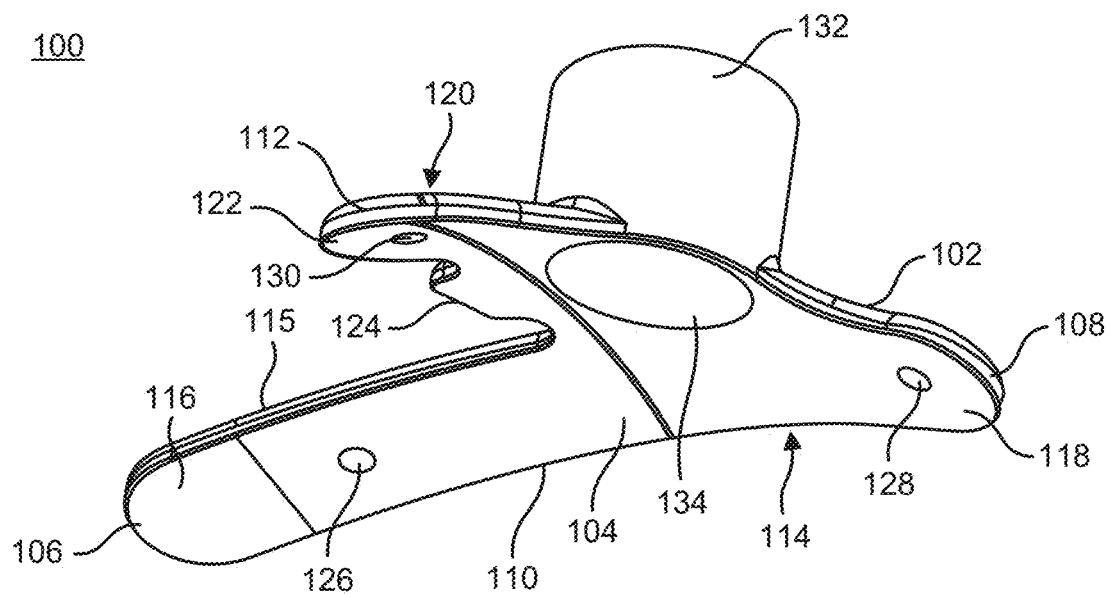
FIG. 4 is a second end, bottom perspective view of the alignment guide of FIG. 1, in accordance with an aspect of the present disclosure.
Figure 5:
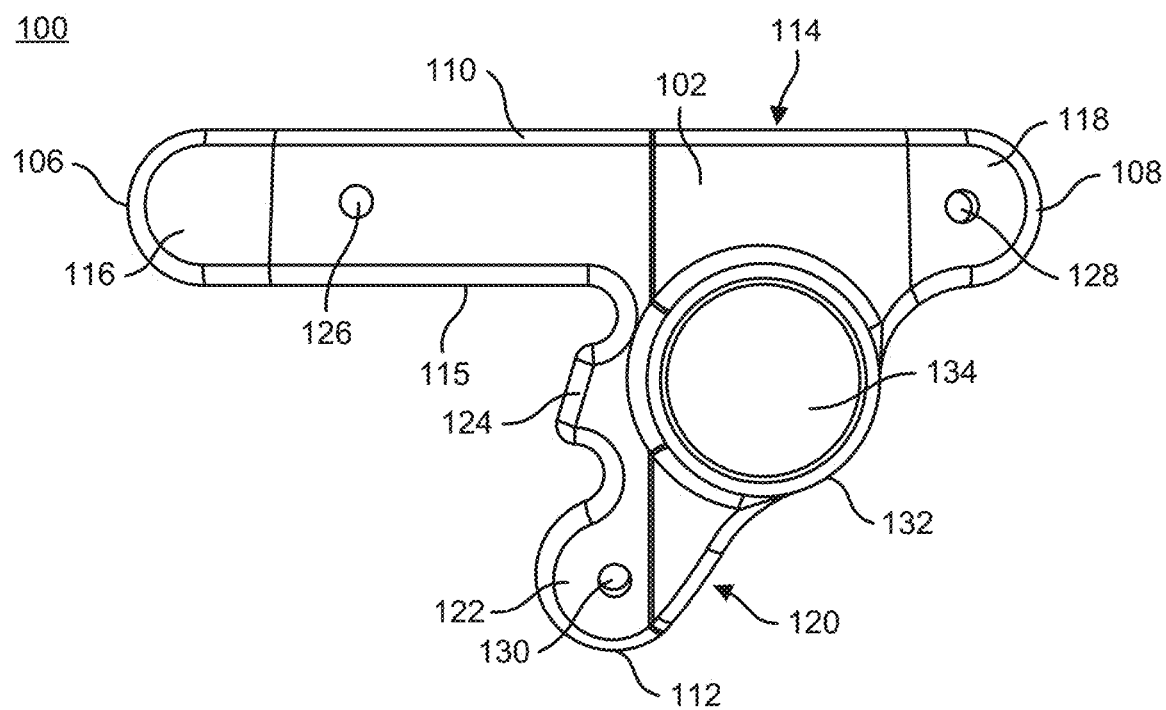
FIG. 5 is a top view of the alignment guide of FIG. 1, in accordance with an aspect of the present disclosure.
Figure 6:
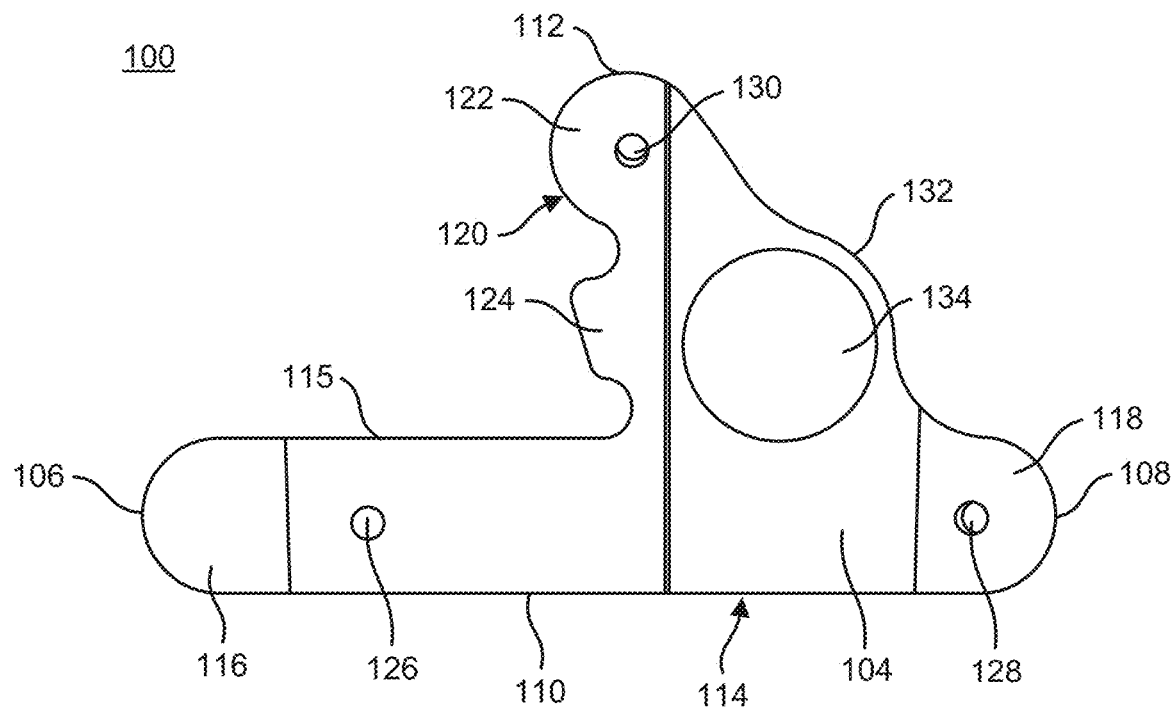
FIG. 6 is a bottom view of the alignment guide of FIG. 1, in accordance with an aspect of the present disclosure.
Figure 7:
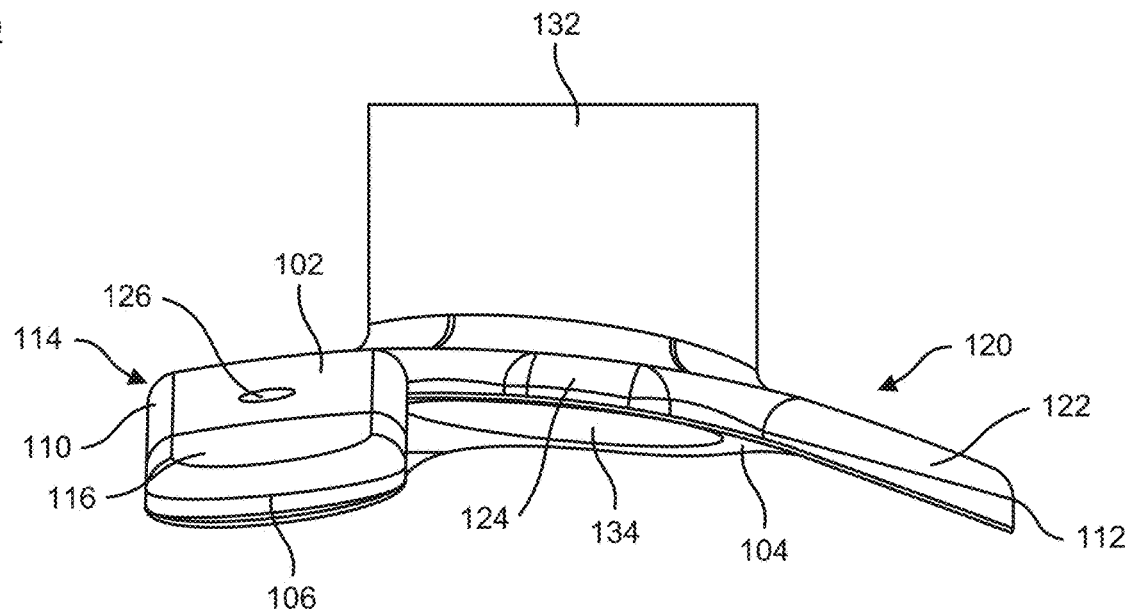
FIG. 7 is a first end elevational view of the alignment guide of FIG. 1, in accordance with an aspect of the present disclosure.
Figure 8:
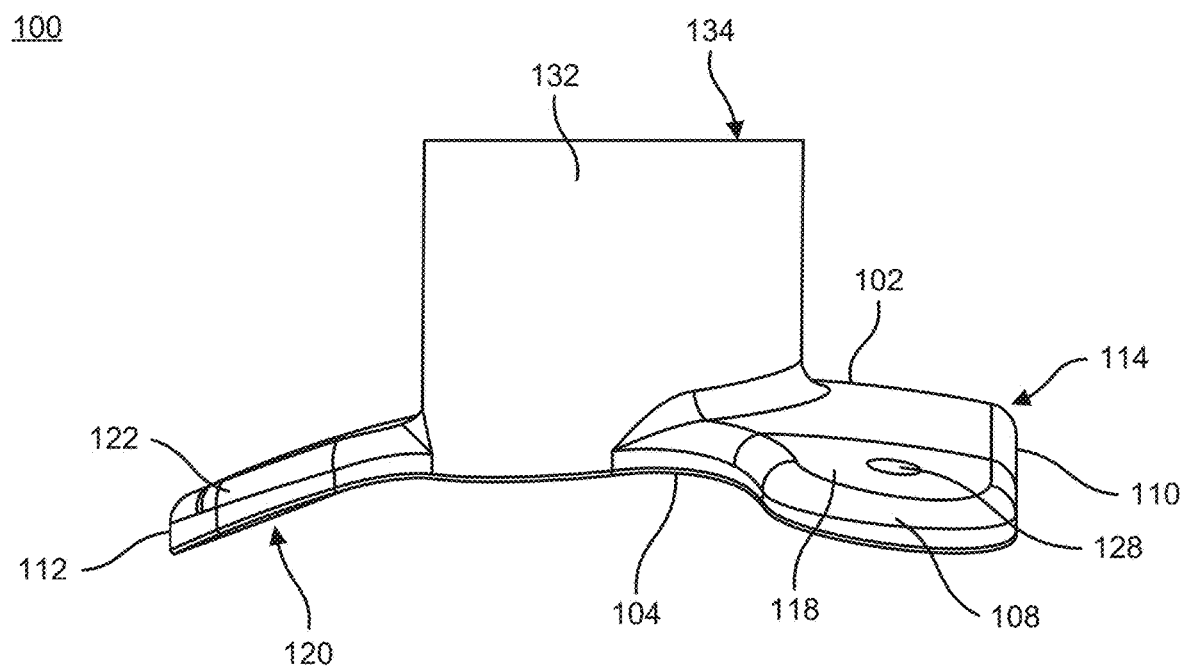
FIG. 8 is a second end elevational view of the alignment guide of FIG. 1, in accordance with an aspect of the present disclosure.
Figure 9:
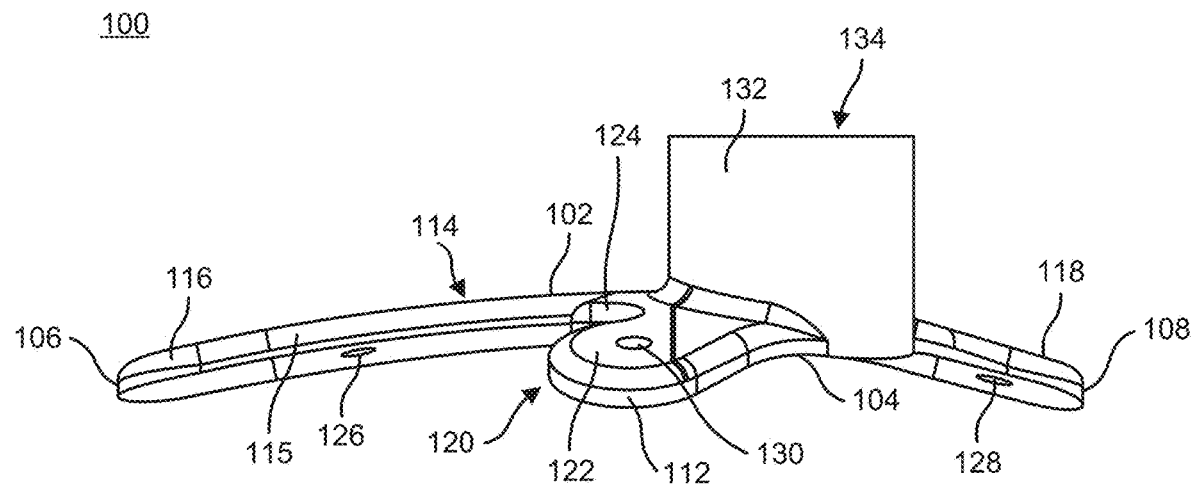
FIG. 9 is a first side elevational view of the alignment guide of FIG. 1, in accordance with an aspect of the present disclosure.
Figure 10:
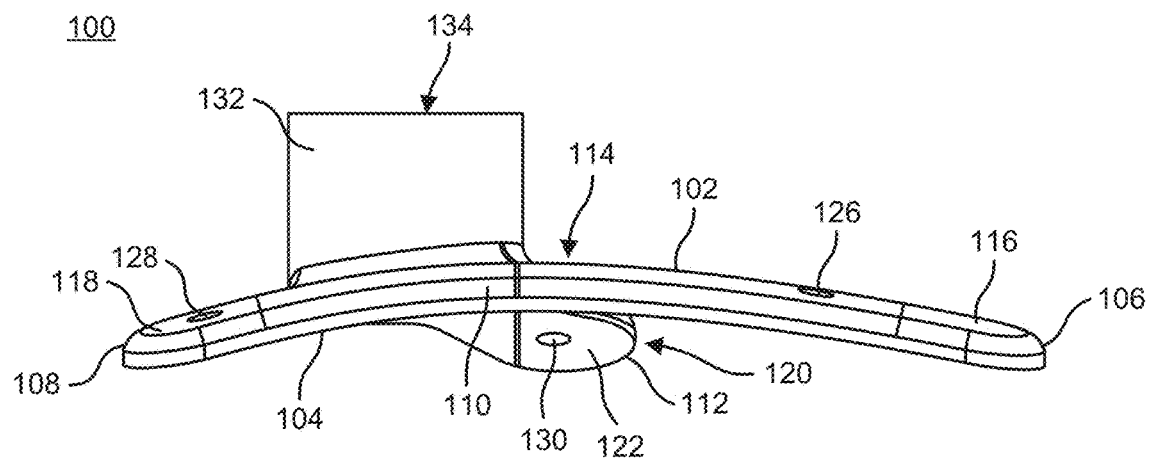
FIG. 10 is a second side elevational view of the alignment guide of FIG. 1, in accordance with an aspect of the present disclosure.

Generally stated, disclosed herein are embodiments of plate templates or reaming guides, implant or plate, and plate system or bone fixation devices. Further, surgical methods for using the devices for fixation of human bones, such as, the foot bones, and to the internal fixation of the proximal portion of metatarsal bones to the bones of the mid-foot and rear-foot to stabilize realignment of a fracture, dislocation, fusion or the like of the tarso-metatarsal joints, mid-foot and rear-foot are discussed.

In this detailed description and the following claims, the words proximal, distal, anterior or plantar, posterior or dorsal, medial, lateral, superior and inferior are defined by their standard usage for indicating a particular part of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current devices and methods are described herein with reference to use with the bones of the foot, the bones of the foot, ankle and lower leg may be used to describe the surfaces, positions, directions or orientations of the devices, instrumentation and methods. Further, the devices and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the devices and methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the devices and methods, and the aspects, components, features and the like thereof, described herein with respect to the right foot may be mirrored so that they likewise function with the left foot. Further, the devices and methods, and the aspects, components, features and the like thereof, disclosed herein are described with respect to the foot for brevity purposes, but it should be understood that the devices and methods may be used with other bones of the body having similar structures, for example the upper extremity, and more specifically, with the bones of the wrist, hand, and arm.

Referring to the drawings, wherein like reference numerals are used to indicate like or analogous components throughout the several views, and with particular reference to FIGS. 1-10, there is illustrated a plate template, alignment guide, reaming guide 100. The plate template 100 may include a top or dorsal surface 102 opposite a bottom or plantar surface 104, a first or proximal end 106 opposite a second or distal end 108, and a first or medial side 110 opposite a second or lateral side 112. The template 100 may be, for example, curved, curvilinear or otherwise arced between the first end 106 and the second end 108. The template 100 may be, for example, further curved, curvilinear or otherwise arced between the first side 110 and the second side 112. The template 100 may be, for example, curved, curvilinear or otherwise arced to match the shape of the bone that the plantar surface 104 of the template 100 will engage.

The plate template 100 may also include a body portion 114 may have a first or medial side 110 and a second or lateral side 115. The body portion 114 may include a first lobe 116, a second lobe 118 and an extension member 120, as shown in FIGS. 1-6. The first lobe 116 may extend, for example, to the proximal end 106 of the template 100. The second lobe 118 may extend, for example, to the distal end 108 of the template 100. The first lobe 116 may have, for example, a length longer than a length of the second lobe 118. The extension member or lateral extension member 120 may extend, for example, from the lateral side 115 of the body member 114 to the lateral side 112 of the plate template 100. The extension member 120 may include a third lobe 122 positioned at the lateral side 112 and a tab 124 positioned between the third lobe 122 and the lateral side 115 of the body portion 114. The first side of the extension member 120 on the proximal end 106 may be, for example, slightly angled from the lateral side 115 of the body portion 114 to the outermost point of the extension member 120 on the lateral side 112 of the template 100 forming a first angle. The second side of the extension member 120 proximate to the distal end 108 may also be, for example, angled from the lateral side 115 of the body portion 114 at a position near the distal end 108 to the outermost point on the lateral side 112 of the template 100 forming a second angle. The first and second angles may be, for example, measured from the lateral side 115 of the body portion 114 and the second angle may be larger than the first angle. The extension member 120 may also have, for example, a length measured between the lateral side 115 of the body portion 114 and the lateral side 112 of the template 100. The length of the extension member 120 may be, for example, longer than the length of the second lobe 118 and shorter than the length of the first lobe 116.

With continued reference to FIGS. 1-6, the template 100 also includes a plurality of through holes 126, 128, 130. The through holes 126, 128, 130 may be, for example, sized and shaped or configured to receive a wire, for example, a k-wire, guide wire, olive wire, or the like, to secure the template 100 to a patient's bones. As shown, the template 100 may include, for example, a first through hole 126 positioned between the first or proximal end 106 and a midpoint of the body portion 114 of the template 100. The template 100 may also include, for example, a second through hole 128 positioned near the second or distal end 108 of the template 100. Further, the template 100 may include, for example, a third through hole 130 positioned in the third lobe 122 near the lateral side 112 of the template 100, near an end of the extension member 120. The through holes 126, 128, 130 may be, for example, straight or angled as they extend between the top surface 102 and the bottom surface 104 of the template 100.

As shown in FIGS. 1-10, the template 100 may further include a reamer guide 132 extending away from the top surface 102 of the template 100. The reamer guide 132 may be, for example, positioned on the extension member 120 between the body portion 114 and the third lobe 122. The reamer guide 132 may also be positioned, for example, adjacent to the tab 124. A center of the reamer guide 132 may be positioned, for example, a set distance from a proximal edge of the tab 124. The distance between the center of the reamer guide 132 and the proximal edge of the tab 124 may be, for example, approximately 0.5 cm to 3 cm and more specifically, approximately 1 cm. The reamer guide 132 may have, for example, a circular or round shape. The reamer guide 132 may also include a through hole or reamer hole 134. The reamer hole 134 may extend from a top surface of the reamer guide 132 through the reamer guide 132 to a bottom surface 104 of the template 100. The reamer guide 132 may be, for example, sized and shaped or configured to receive a separate reamer instrument, as discussed in greater detail below with respect to FIGS. 27 and 28.

Referring now to FIGS. 11-18, an implant or plate 200 is shown. The implant 200 includes a top or dorsal surface 202 opposite a bottom or plantar surface 204, a first or proximal end 206 opposite a second or distal end 208, and a first or medial side 210 opposite a second or lateral side 212. The implant 200 may be, for example, curved, curvilinear or otherwise arced between the first end 206 and the second end 208. The implant 200 may be, for example, further curved, curvilinear or otherwise arced between the first side 210 and the second side 212. The implant 200 may be, for example, curved, curvilinear or otherwise arced to match the shape of the bone that the plantar surface 204 of the implant 200 will engage.

Figure 13:
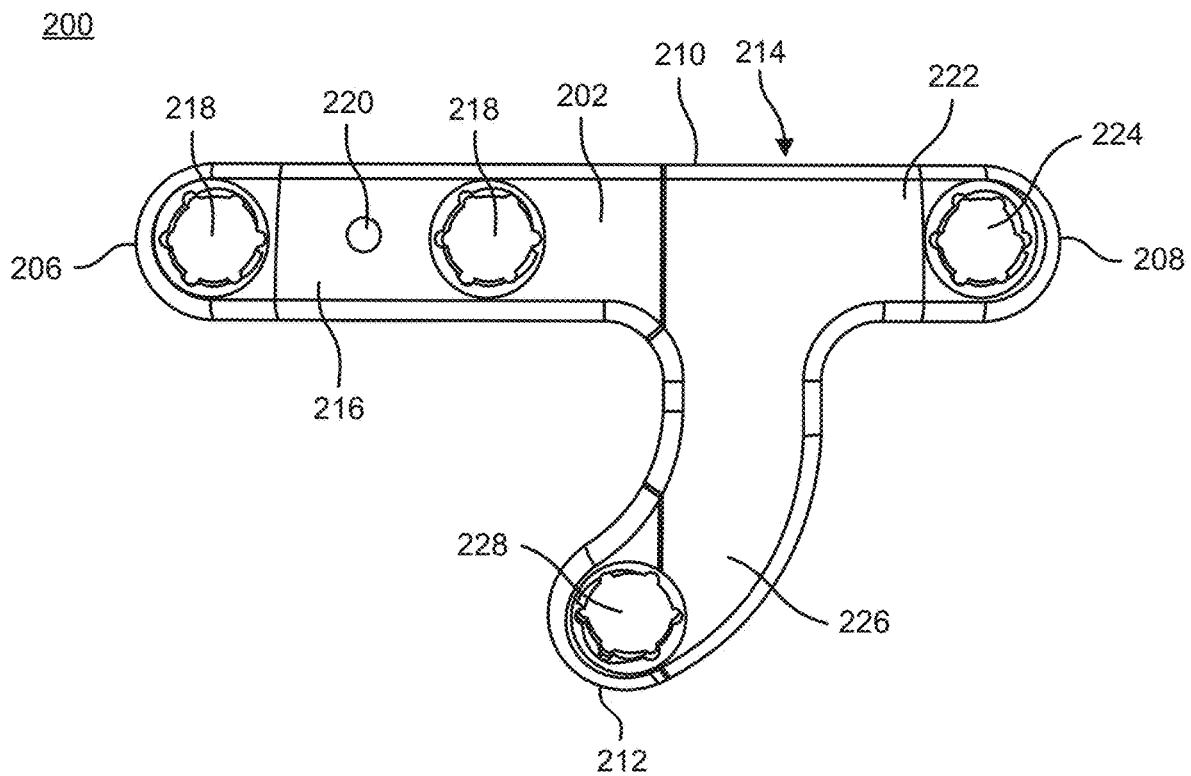
FIG. 13 is a top view of the implant of FIG. 11, in accordance with an aspect of the present disclosure.
Figure 14:
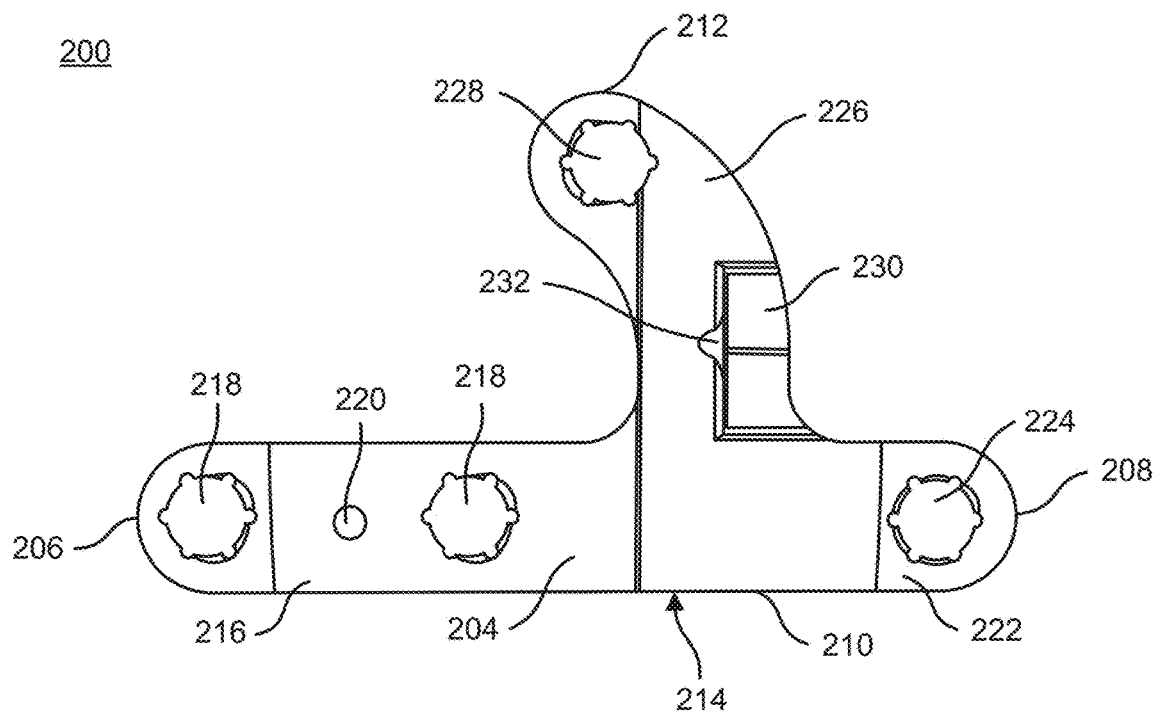
FIG. 14 is a bottom view of the implant of FIG. 11, in accordance with an aspect of the present disclosure.

The implant 200 may also include a body portion 214 with a first or proximal arm 216, a second or distal arm 222, and a third or lateral arm 226. The first arm 216 may extend, for example, to the proximal end 206 of the implant 200. The second arm 222 may extend, for example, to the distal end 208 of the implant 200. The third arm 226 may extend, for example, away from the body portion 214 to the lateral side 212. As shown in FIGS. 13 and 14, the third arm 226 may be, for example, curved or arced toward the proximal end 206 as the third arm 226 extends away from the body portion 214. The implant 200 may also include an extension member or plantar extension member 230 extending away from the bottom surface 204 of the third arm 226. The extension member 230 may be positioned, for example, adjacent to the body portion 214 and aligned with the distal edge of the third arm 226. The first arm 216 may be, for example, longer than the second arm 222.

The first arm 216 may include, for example, at least one first fastener hole 218 and a through hole or wire hole 220, as shown in FIGS. 11-14. The at least one first fastener hole 218 extends from the top surface 202 through the bottom surface 204. As shown, the at least one first fastener hole 218 may be, for example two fastener holes 218. For example, one first fastener hole 218 may be positioned at the first end 206 and a second first fastener hole 218 may be positioned between the one first fastener hole 218 and a midpoint along the longitudinal axis of the implant 200. The fastener holes 218 may be, for example, sized and shaped or configured to receive a bone fastener, bone screw, or the like for coupling the implant 200 to the bones of a patient, as described in greater detail below. The fastener holes 218 may be, for example, threaded on an interior surface of the holes 218. The threads of both holes 218 may include, for example, at least one scallop or cutout forming a break in the threads. The threads and at least one cutout may be configured or shaped to lock a fastener or screw (not shown) in the holes 218. The through hole 220 may be, for example, positioned between the one first fastener hole 218 and the second first fastener hole 218. The through hole 220 may be, for example sized and shaped or configured to receive a wire, for example, a k-wire, guide wire, olive wire or the like for positioning the implant 200 onto a patient's foot, as described in greater detail below.

The second arm 222 may also include, for example, at least one second fastener hole 224, as shown in FIGS. 11-14. The at least one second fastener hole 224 extends from the top surface 202 through the bottom surface 204. As shown, the at least one second fastener hole 224 may be, for example, one second fastener hole 224 positioned at the distal end 208 of the implant 200. The one second fastener hole 224 may be, for example, sized and shaped or configured to receive a bone fastener, bone screw, or the like for coupling the implant 200 to the bones of a patient, as described in greater detail below. The one second fastener hole 224 may be, for example, threaded on an interior surface of the hole 224. The threads may include, for example, at least one scallop or cutout forming a break in the threads. The threads and at least one cutout may be configured or shaped to lock a fastener or screw (not shown) in the hole 224.

With continued reference to FIGS. 11-14, the third arm 226 may also include at least one third fastener hole 228. The at least one third fastener hole 228 extends from the top surface 202 through the bottom surface 204. As shown, the at least one third fastener hole 228 may be, for example, one third fastener hole 228 positioned at the end of the third arm 226 on the lateral side 212 of the implant 200. The fastener hole 228 may be, for example, sized and shaped or configured to receive a bone fastener, bone screw, or the like for coupling the implant 200 to the bones of a patient, as described in greater detail below. The fastener hole 228 may be, for example, threaded on an interior surface of the holes 228. The threads may include, for example, at least one scallop or cutout forming a break in the threads. The threads and at least one cutout may be configured or shaped to lock a fastener or screw (not shown) in the hole 228.

Figure 11:
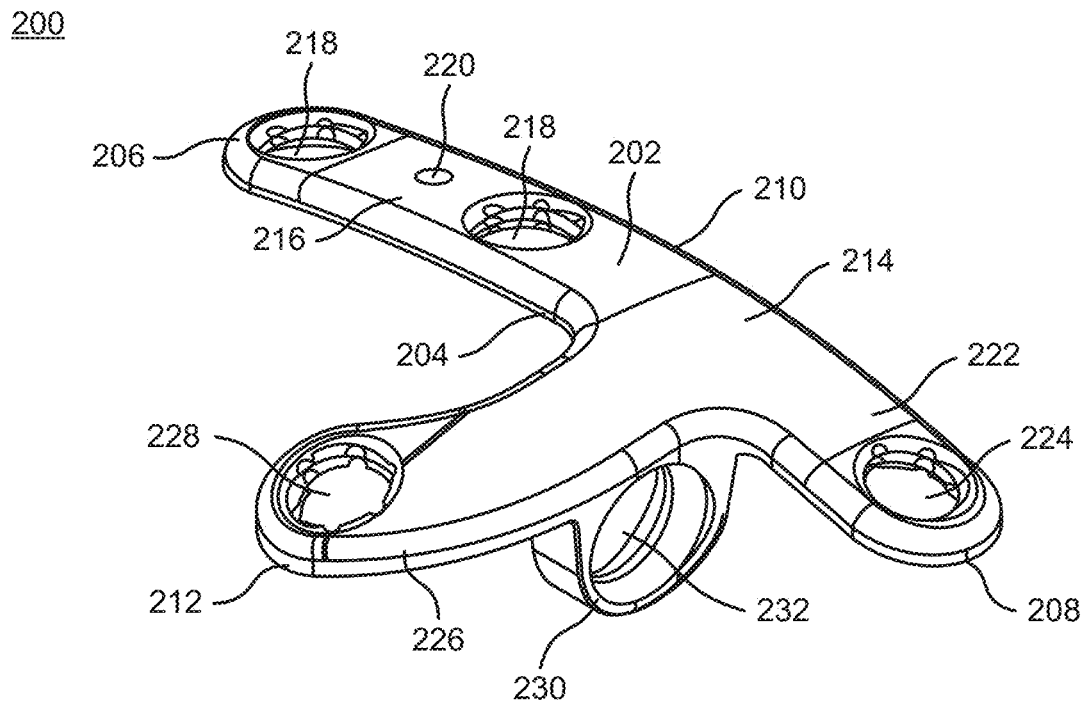
FIG. 11 is a top perspective view of an implant, in accordance with an aspect of the present disclosure.
Figure 12:
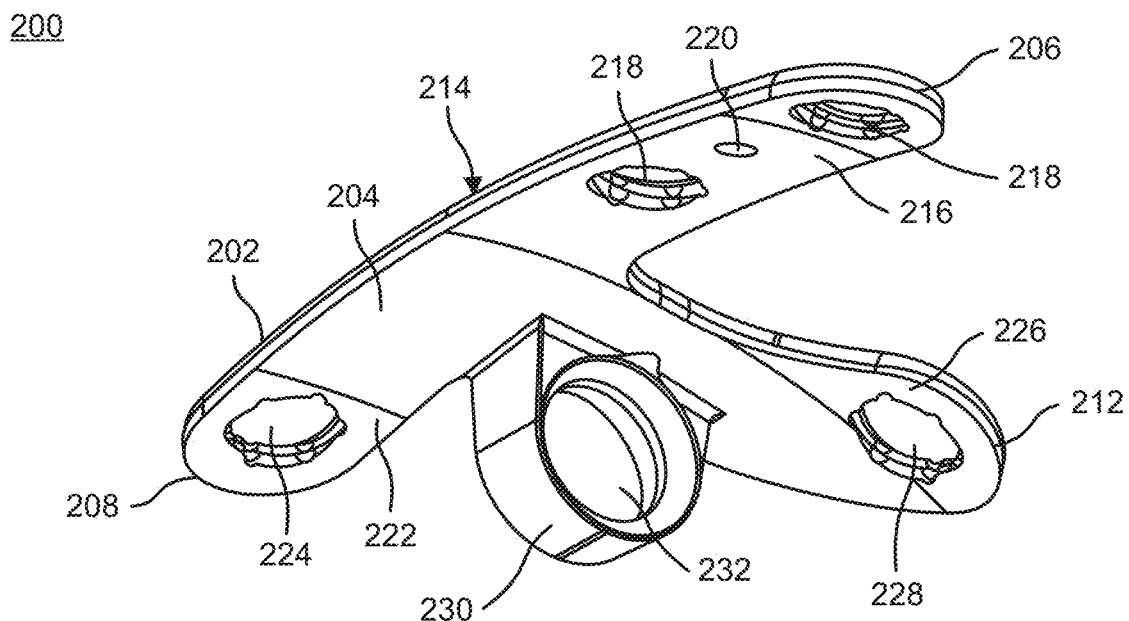
FIG. 12 is a bottom perspective view of the implant of FIG. 11, in accordance with an aspect of the present disclosure.
Figure 15:
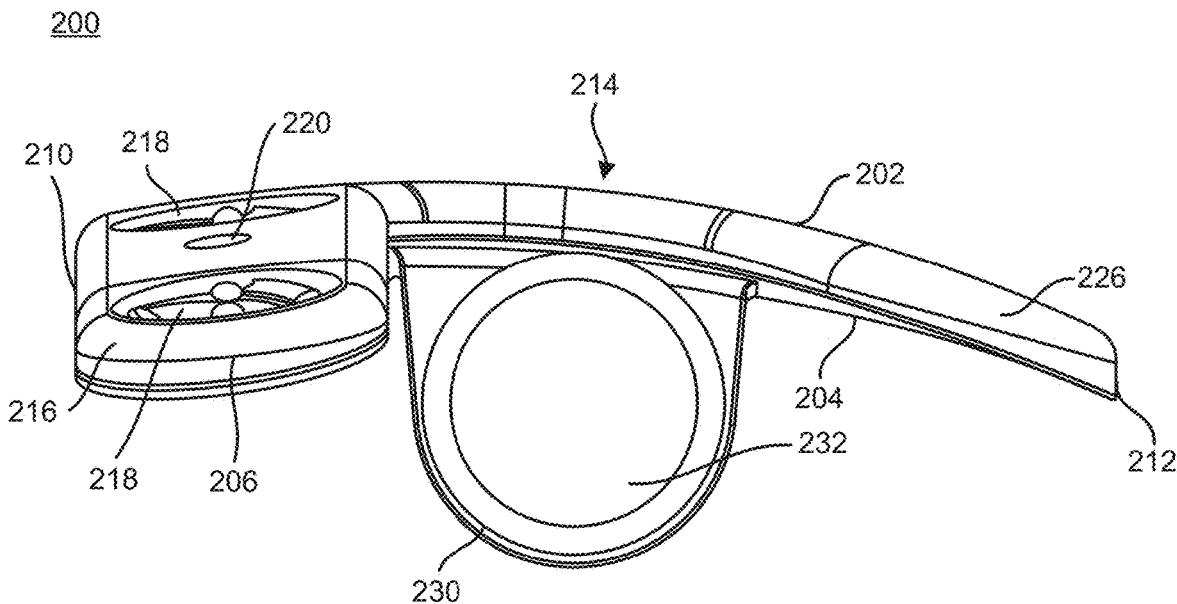
FIG. 15 is a first end elevational view of the implant of FIG. 11, in accordance with an aspect of the present disclosure.
Figure 16:
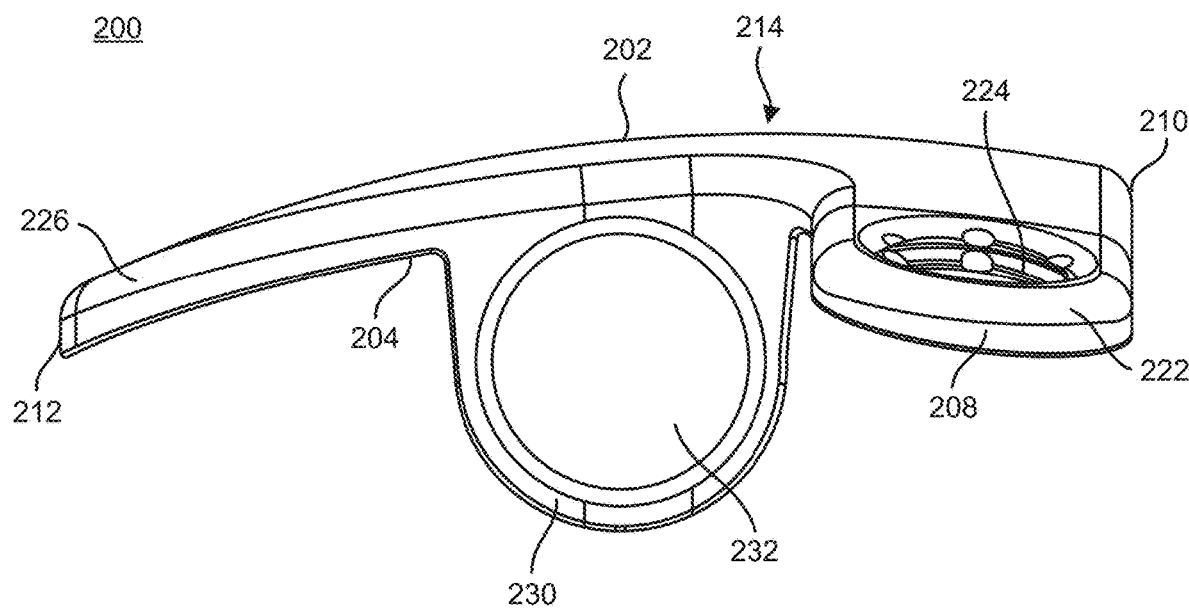
FIG. 16 is a second end elevational view of the implant of FIG. 11, in accordance with an aspect of the present disclosure.
Figure 17:
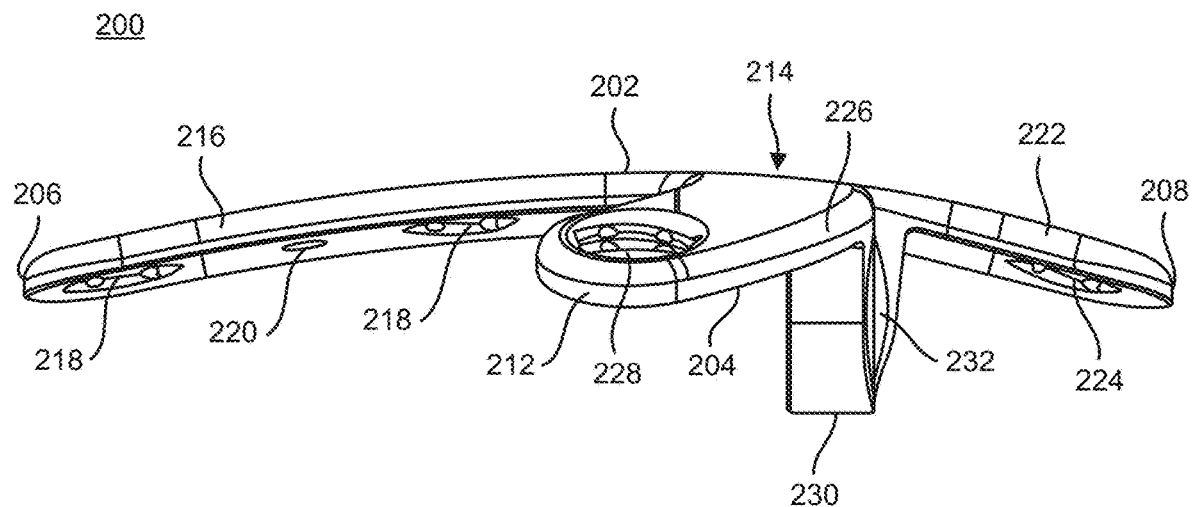
FIG. 17 is a first side elevational view of the implant of FIG. 11, in accordance with an aspect of the present disclosure.
Figure 18:
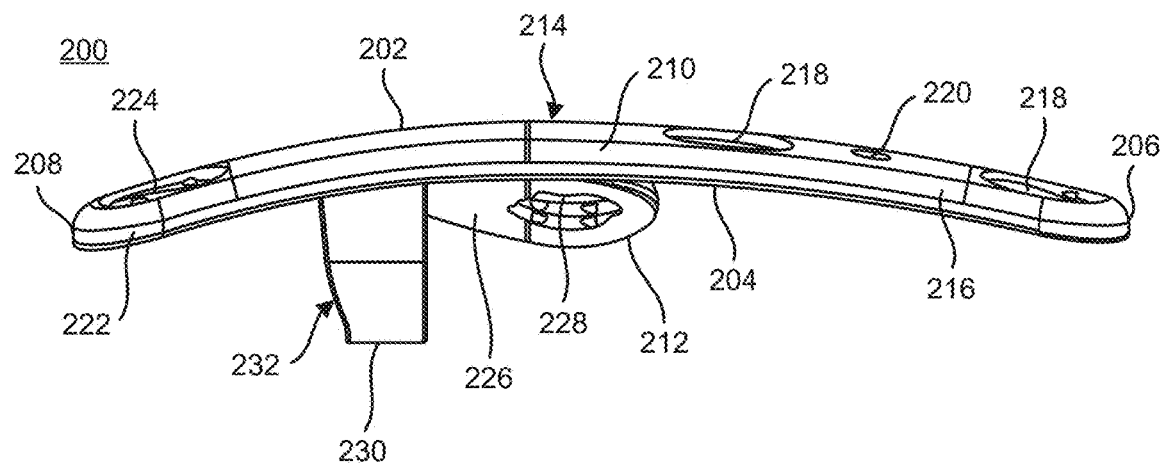
FIG. 18 is a second side elevational view of the implant of FIG. 11, in accordance with an aspect of the present disclosure.

Referring now to FIGS. 11, 12, 15 and 16, the extension member 230 may include a hole or screw hole 232. The hole 232 may extend, for example, through the extension member 230 in a proximal-distal direction, as shown in FIGS. 11 and 12. The hole 232 may be positioned to extend, for example, through the center of the extension member 230, although alternative positions for the hole 232 are also contemplated. The hole 232 may be, for example, sized and shaped or configured to receive a bone fastener, bone screw, beaming screw, pin, rod, or the like for coupling the implant 200 to the bones of a patient, as described in greater detail below. In one embodiment, the hole 232 may be, for example, threaded on an interior surface of the hole 232. The threads may include, for example, at least one scallop or cutout (not shown) forming a break in the threads. The threads and at least one cutout may be configured or shaped to lock a fastener or screw (not shown) in the hole 232. It is further understood that the interior surface of the hole 232 may be smooth or threadless. As shown in FIGS. 17 and 18, the extension member 230 may be, for example, shaped to be recessed into a patient's bones and/or joint. The extension member 230 may include, for example, a first side positioned facing the proximal end 206 of the implant 200, which may be planar. The extension member 230 may also include, for example, a second side positioned facing the distal end 208 of the implant 200 and the second side may be curved as it extends in a dorsal-plantar direction. The second side of the extension member 230 may also be, for example, curved in a medial-lateral direction. The curvature in the medial-lateral direction may, for example, match the curvature of the plate 200 at the point where the body portion 214 engages the third arm 226. As shown in FIG. 18, the extension member 230 may, for example, taper from the bottom surface 204 of the implant 200 in a dorsal-plantar direction. In addition, as shown in FIGS. 15 and 16, the extension member 230 may be tapered in medial-lateral direction as it extends away from the bottom surface 204 of the implant 200. Further, the peripheral outer surface of 230 extending between the first side and the second side may be, for example, curved to facilitate insertion and avoid impingement.

Figure 19:
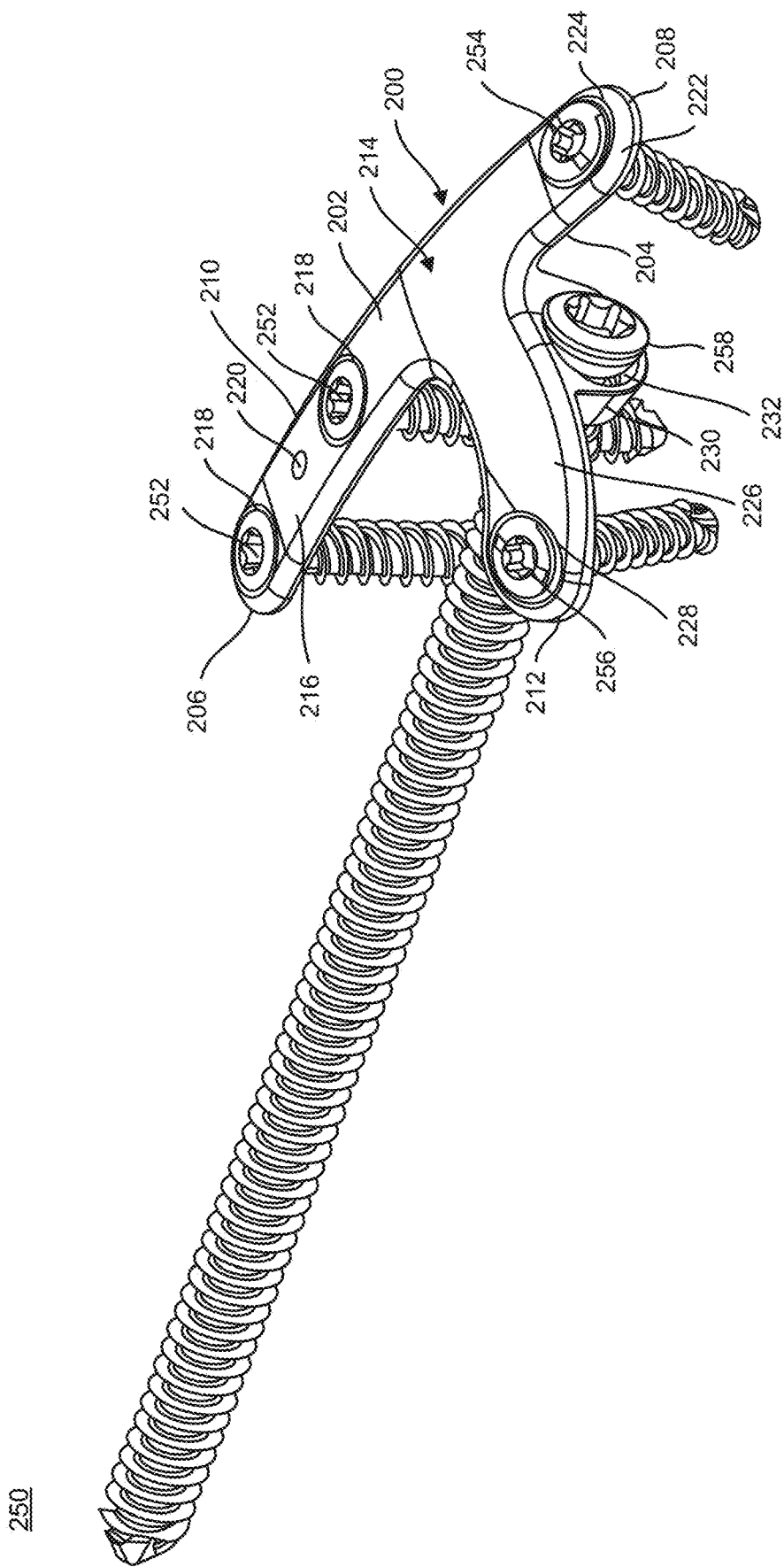
FIG. 19 is a top perspective view of a plate system, in accordance with an aspect of the present disclosure.

A plate system or bone fixation device 250 is shown in FIG. 19. The plate system 250 includes the implant 200, fasteners 252, 254, 256 and a beam fastener 258. Each component of the plate system 250 may be made from, for example, a biocompatible material, including but not limited to a metal, polymer, composite, etc. With respect to the fasteners 252, 254, 256, the terms "fastener," "bone screw," "fixator," "bone screw," and "screw" may be used interchangeably herein as they essentially describe the same type of device. With respect to fastener 258, the terms "fastener," "beam fastener," "bone screw," "beam screw," "fixator," "elongate member," "rod," and "screw" may be used interchangeably herein as they essentially describe the same type of device. As shown in FIG. 19, the plate system 250 may include a one first fastener 252 inserted into the one first fastener hole 218, a second first fastener 252 inserted into the second first fastener hole 218, a second fastener 254 inserted into the second fastener hole 224, and a third fastener 256 inserted into the third fastener hole 228. In addition, the beam fastener 258 may be inserted through the hole 232 in the extension member 230.

With continued reference to FIG. 19, the fasteners 252, 254, 256, 258 may include a head portion and a shaft portion. The head portion may include a superior end and an inferior end. The superior end of the head portion may have a tool engagement opening, as shown in FIG. 19. The tool engagement opening may have a multi-lobed shape, although other polygonal shapes are also contemplated, including a hexagonal shape. The fasteners 252, 254, 256, 258 may also have a cannulated opening (not shown) extending from the tool engagement opening through the entire length of the fasteners 252, 254, 256, 258. The inferior end of the head portion may optionally be threaded to engage corresponding threads in the holes 218, 224, 228, 232. The inferior end of the head portion is coupled to an end of the shaft portion. The shaft portion may be, for example, threaded along the entire length of the fasteners 252, 254, 256, 258 or only along a portion. The fasteners 252, 254, 256, 258 may be, for example, available in multiple sizes with threaded sections of various lengths, including, for example, a fully threaded shaft portion. The length of the threaded section may correspond to the orientation of insertion into the patient's bones and the bones that the fastener 252, 254, 256 is inserted through and into. The threaded section of the shaft portion may also include a tip. The tip may be, for example, blunt or include at least one cutting thread or be self-tapping thread to assist in insertion into the patient's bone.

Figure 28:
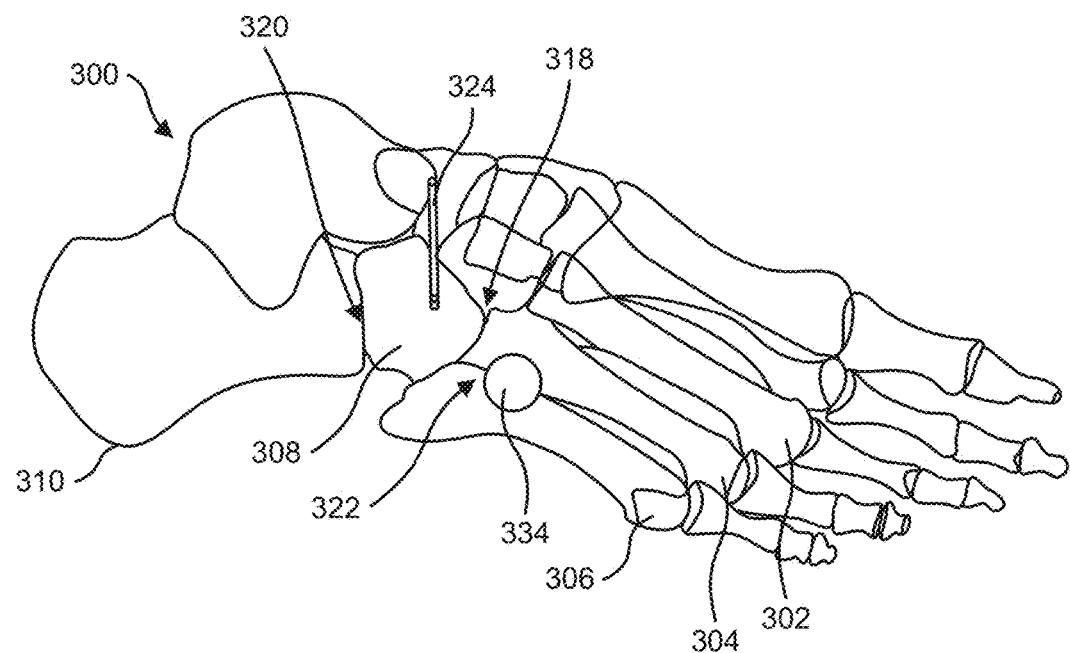
FIG. 28 is an top perspective view of the foot of FIG. 27 after the removal of the reamer, two of the fixation wires, and the alignment guide, showing the reamed portion of the bones, in accordance with an aspect of the present disclosure.
Figure 31:
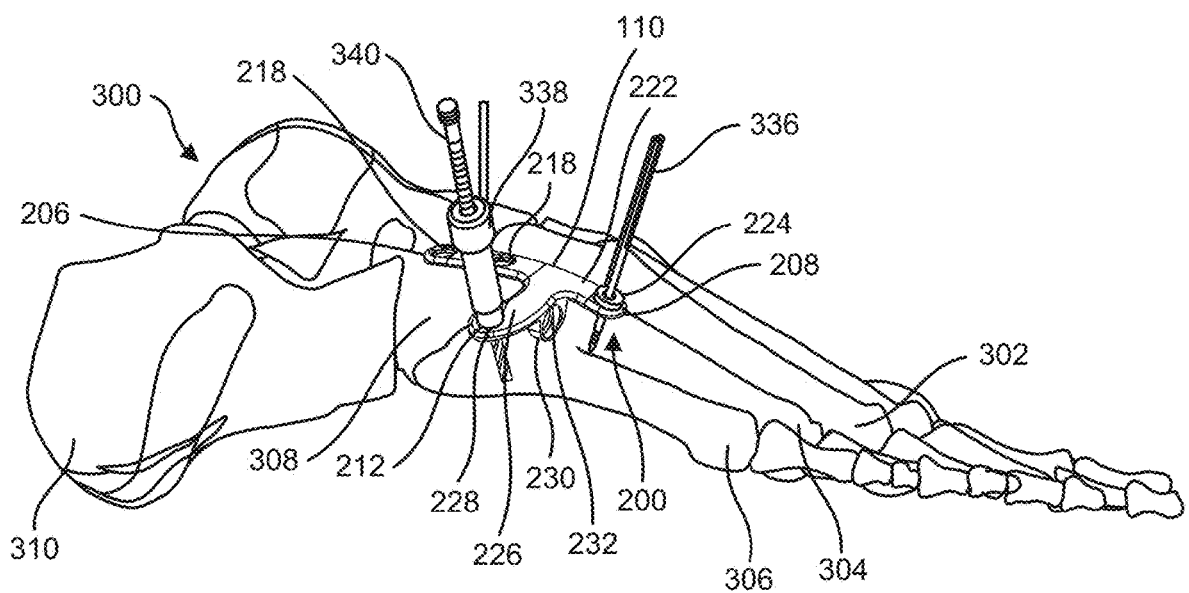
FIG. 31 is a top perspective view of the foot of FIG. 30 after an olive wire is inserted into the foot through the implant, a drill guide is coupled to the implant, and a drill is inserted through the drill guide into the foot, in accordance with an aspect of the present disclosure.
Figure 33:
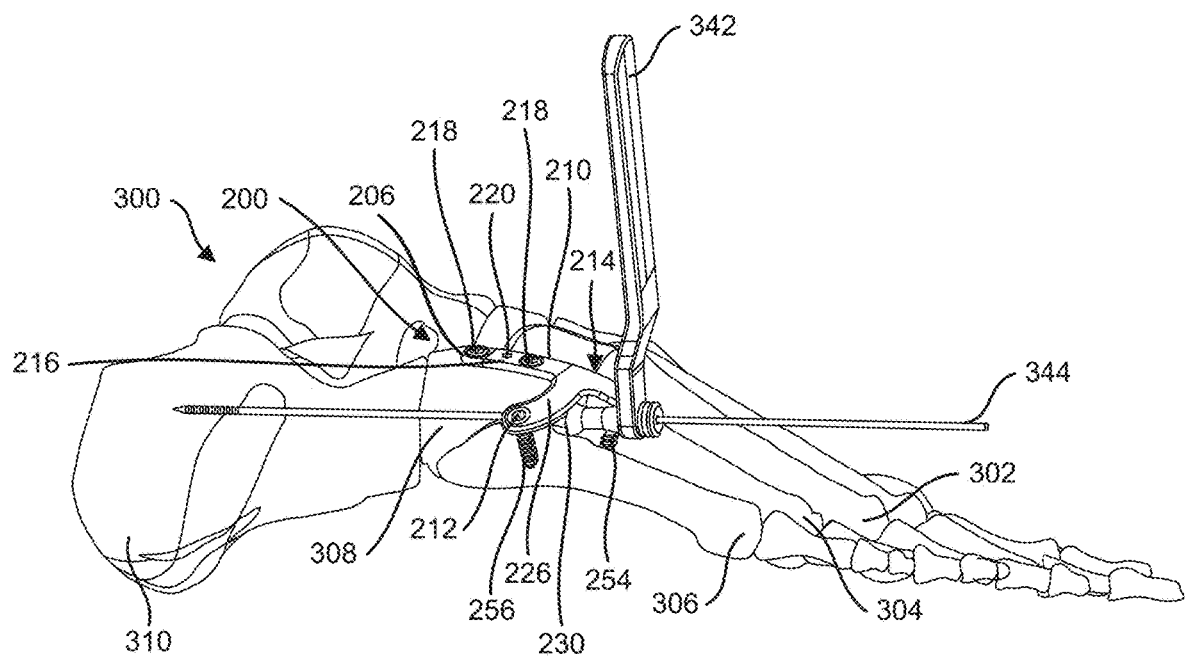
FIG. 33 is a side perspective view of the foot of FIG. 32 after coupling a k-wire guide to the implant and inserting a k-wire through the k-wire guide and into the foot, in accordance with an aspect of the present disclosure.
Figure 38:
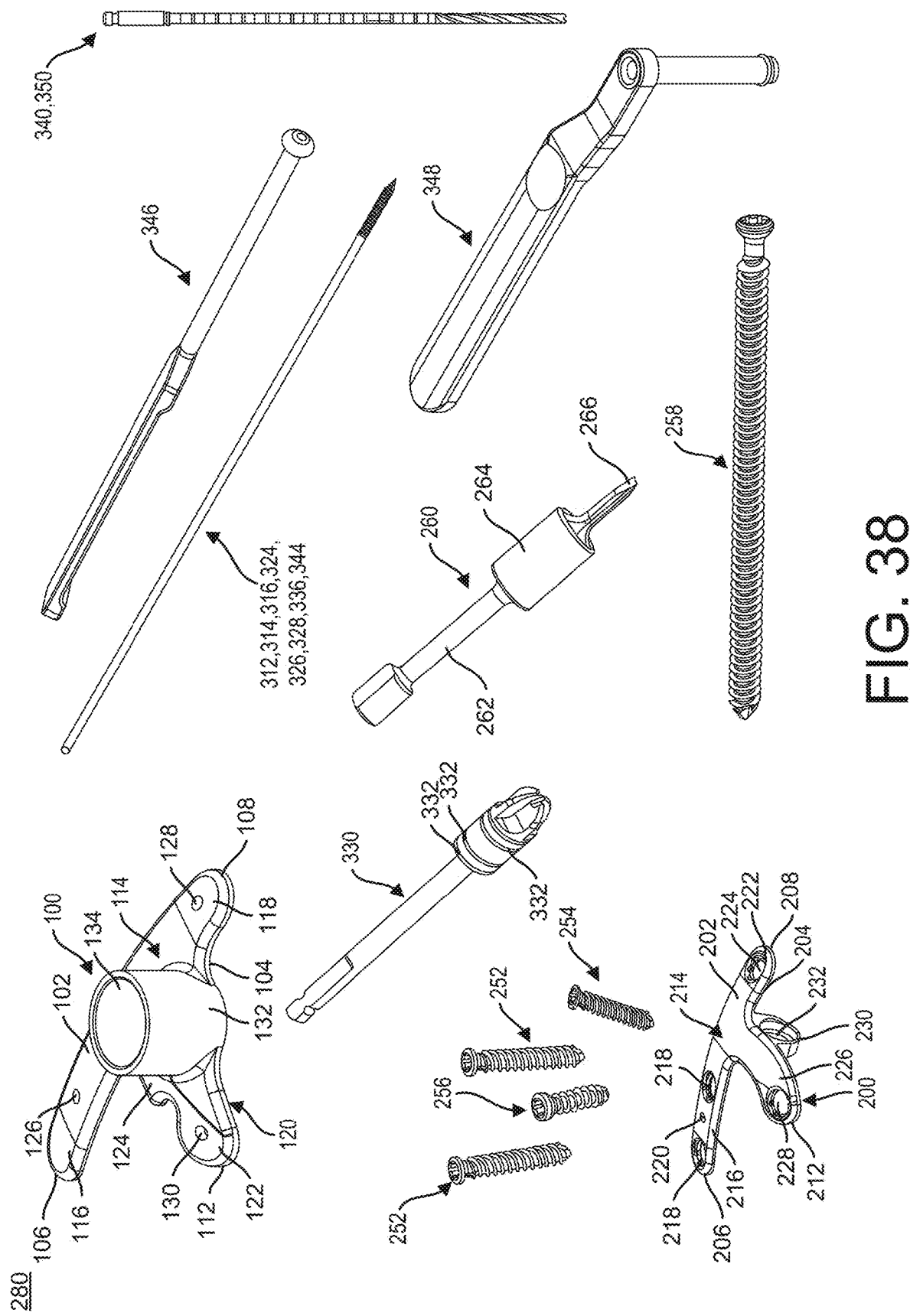
FIG. 38 is a perspective view of a fusion system with the template of FIG. 1, the plate system of FIG. 19, a joint preparation paddle, a reamer, a wire, a drill bit, a cannulated depth gauge and a soft tissue protector, in accordance with an aspect of the present disclosure.

As shown in FIG. 38, an implant kit or fusion system 280 may include at least one plate template 100, at least one plate 200, a plurality of fasteners 252, 254, 256, and at least one beam fastener 258. The fusion system may also include at least one joint preparation paddle 260, and at least one reamer 330. The fusion system may also include, a plurality of wires 312, 314, 316, 324, 326, 328, 336, 344, at least one drill guide 338s as shown in FIG. 31, at least one drill bit 340, 350, a k-wire guide 342 as shown in FIG. 33, a cannulated depth gauge 346, and a soft tissue protector 348. The plurality of wires 312, 314, 316, 324, 326, 328, 336, 344 may be, for example, threaded or non-threaded wires, guide wires, k-wires, olive wires, or other temporary fixation members as known by one of ordinary skill in the art. A sample wire 312, 314, 316, 324, 326, 328, 336, 344 is shown in FIG. 28.

Figure 20:
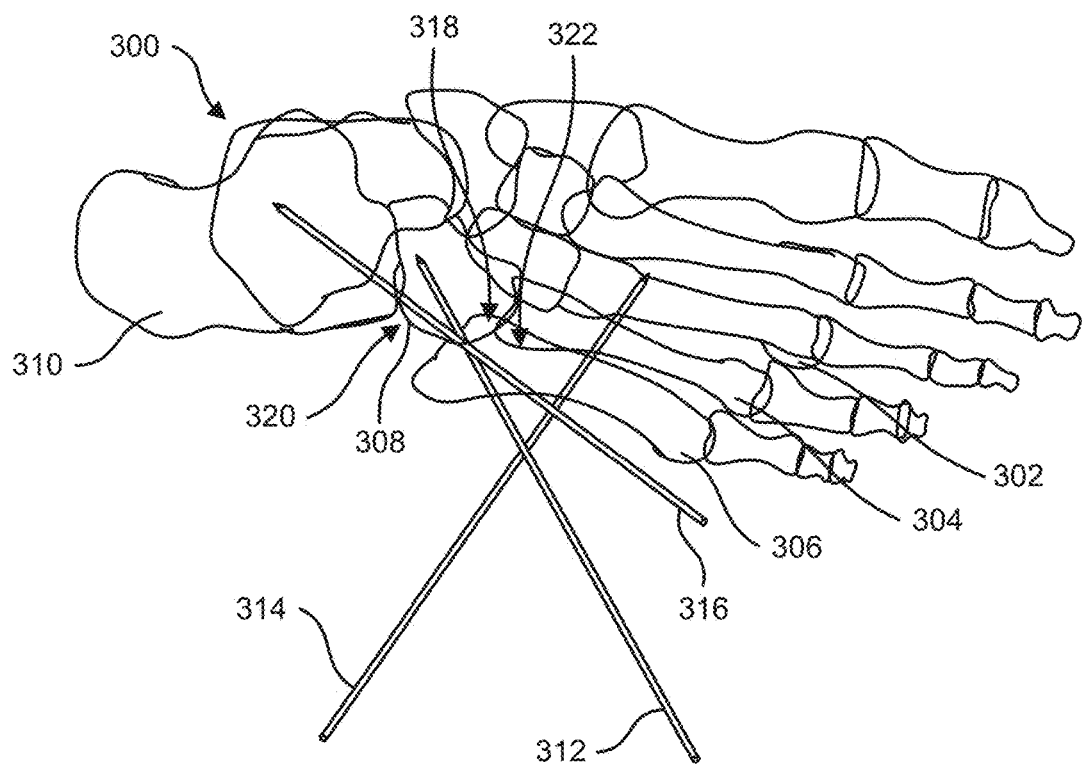
FIG. 20 is a top perspective view of a foot with temporary fixation members positioned within the target bones, in accordance with an aspect of the present disclosure.

Referring now to FIGS. 20-37, one embodiment of a surgical method of using the plate template 100 and plate system 250 is shown. The method may include making an incision over the calcaneocuboid joint 320 proximally and extending past the $4^{th}/5^{th}$ metatarsal-cuboid joints 318. After the incision is made, additional soft tissue dissection may be performed until the joints 318, 320 are accessible. Next, the cartilage may be removed from the $4^{th}/5^{th}$ metatarsal-cuboid joints 318, as well as the calcaneocuboid joint 320 using the surgeon's preferred technique. Once the joint preparation is complete, the joints are realigned to achieve a plantigrade foot. As shown in FIG. 20, the temporary fixation may then occur and may include inserting a first temporary fixator or k-wire 312 from the dorsal fifth metatarsal 306 into the cuboid 308 proximally. Then, a second temporary fixator or k-wire 314 may be placed across the fifth metatarsal 306, fourth metatarsal 304, and third metatarsal 302. Finally, a third temporary fixator or k-wire 316 may be placed to stabilize the cuboid 308 to the calcaneus 310. It is also contemplated that if necessary due to bone quality and/or surgeon preference, placement of the temporary fixators 312, 314, 316 may be altered as would be understood by one of ordinary skill in the art to achieve temporary fixation of the calcaneocuboid joint 320 and $4^{th}/5^{th}$ ID metatarsal-cuboid joints 318. Referring now to FIGS. 21-36, the wires 312, 314, 316 are not shown for ease of viewing, however, the wires 312, 314, 316 are still inserted in the foot 300 during the steps illustrated in these figures and removed during the technique once those particular bones and/or joints are stabilized.

Figure 21:
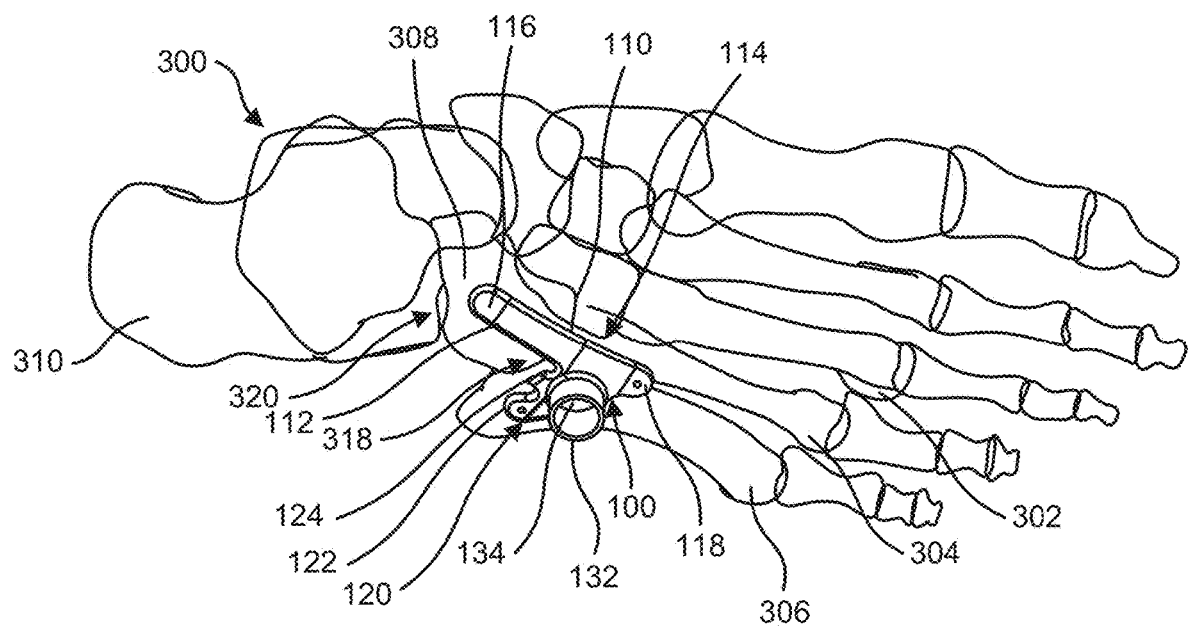
FIG. 21 is a top perspective view of the foot of FIG. 20 with the alignment guide of FIG. 1 positioned on the foot, in accordance with an aspect of the present disclosure.
Figure 22:
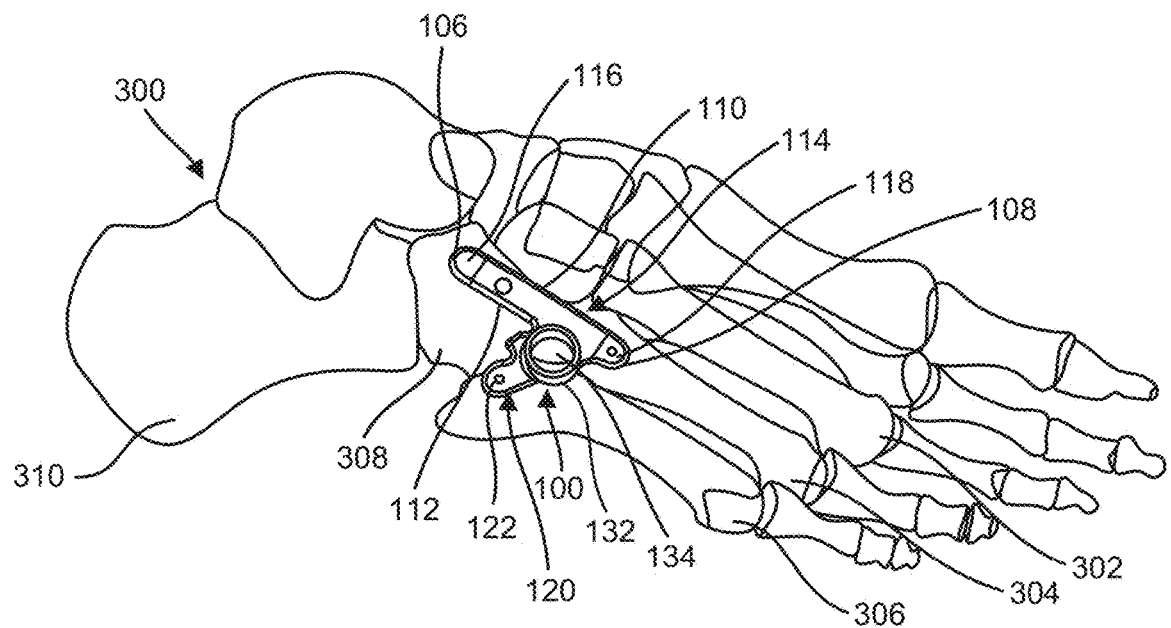
FIG. 22 is a side perspective view of FIG. 21, in accordance with an aspect of the present disclosure.
Figure 23:
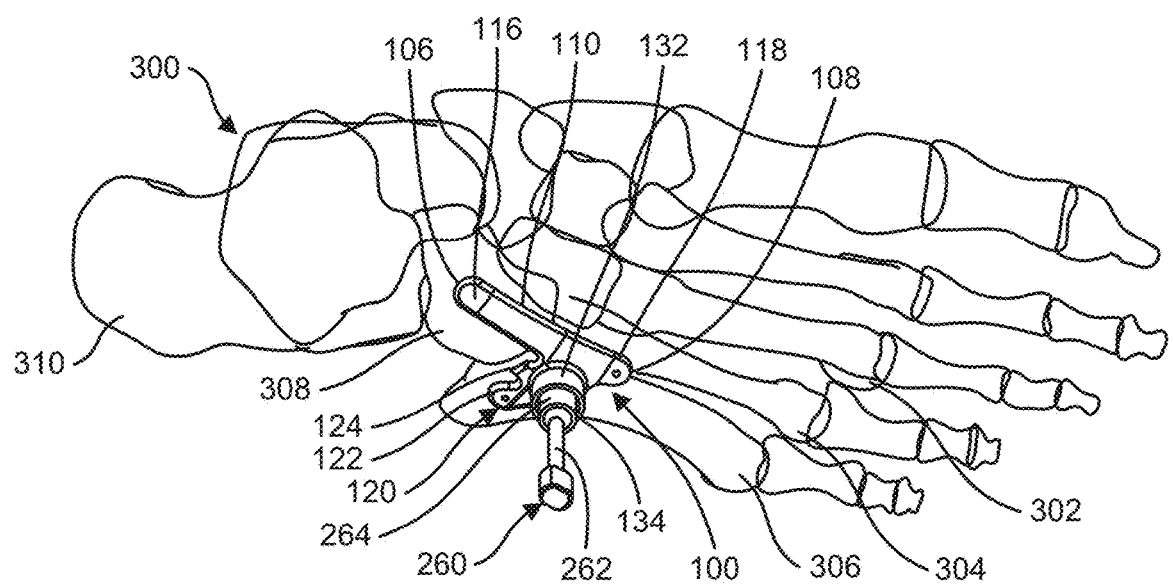
FIG. 23 is a top perspective view of the foot and alignment guide of FIG. 21 with a joint preparation paddle inserted into the alignment guide, in accordance with an aspect of the present disclosure.
Figure 24:
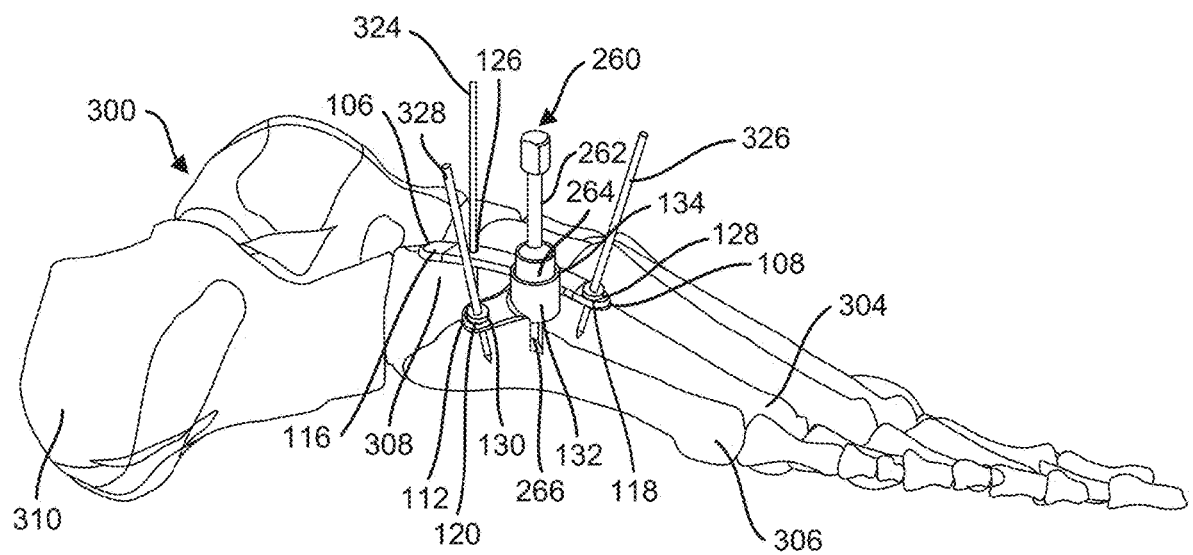
FIG. 24 is a side perspective view of the foot of FIG. 23 with fixation wires inserted through the alignment guide and into the foot, in accordance with an aspect of the present disclosure.

Referring now to FIGS. 21 and 22, the method may include selecting the desired size of the plate template 100 and positioning the template 100 over the cuboid 308, fifth metatarsal 306 and fourth metatarsal 304. Specifically, the flat surface of the tab 124 on the proximal portion of the lateral extension member 120 is aligned with the $4^{th}/5^{th}$ metatarsal-cuboid joint 318. Then, the template 100 may be centered generally over the fourth metatarsal 304 and fifth metatarsal 306 and, as shown in FIG. 23, a joint preparation paddle 260 may be placed into the reamer hole 134 of the reamer guide 132 to contact the $4^{th}/5^{th}$ metatarsal-cuboid joint 318. The joint preparation paddle 260 includes a shaft 262, a head portion 264 extending away from a distal end of the shaft 262, and a joint extension member 266 extending away from the distal end of the head portion 264, as shown in FIG. 24. The head portion 264 may be, for example, shaped to fit into the reamer hole 134 of the template 100. The joint extension member 266 may be, for example, shaped to be inserted between two bones, such as, fourth and fifth metatarsals 304, 306 to center the template 100 over the $4^{th}/5^{th}$ metatarsal joint. The tip of the joint extension member 266 may be sharp to transect the ligaments across a joint. The width and thickness of the tip of the joint extension member 266 may be minimized and selected, for example, to provide minimal joint and ligament disruption when inserted between two bones. As the joint preparation paddle 260 is inserted into the reamer hole 134, the surgeon aligns the joint extension member 266 of the paddle 260 parallel to the metatarsals 304, 306 and pushes the paddle 260 into the intermetatarsal joint 322 to center the template 100, as shown in FIGS. 23 and 24. The template 100 and paddle 260 may be used to position the starting point of a screw, for example, 1 cm from the $4^{th}/5^{th}$ metatarsal-cuboid joint 318 and centered for reaming between the fourth and fifth metatarsals, 304, 306.

Figure 25:
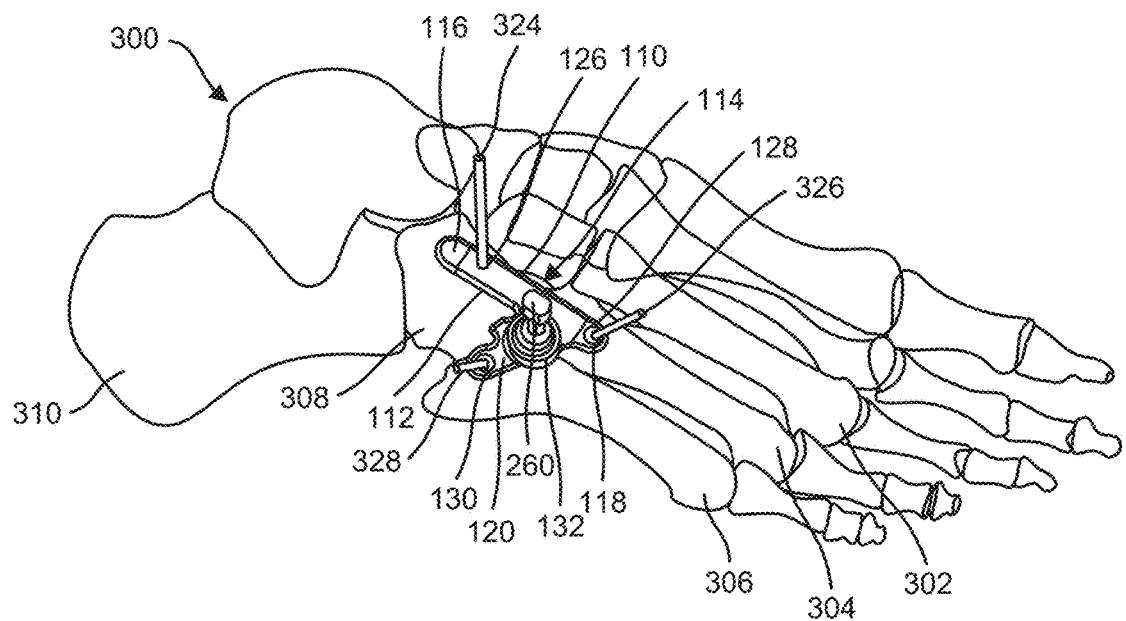
FIG. 25 is a top perspective view of the foot of FIG. 24, in accordance with an aspect of the present disclosure.

Referring now to FIGS. 24 and 25, the method may also include inserting a first wire 324, for example, a threaded k-wire, into the cuboid 308 through the hole 126 in the proximal aspect or proximal end 106 of the template 100. Next, a second wire 326, for example, a threaded olive wire, may be inserted into the fourth metatarsal 304 through the hole 128 in the distal end 108 of the template 100. In addition, a third wire 328, for example, a threaded olive wire, may be inserted into the fifth metatarsal 306 through the hole 130 in the lateral extension member 120. Although non-threaded k-wires and olive wires are contemplated, threaded k-wires and olive wires are preferred to assist with preventing back-out of the template 100 while reaming the bones 304, 306.

Figure 26:
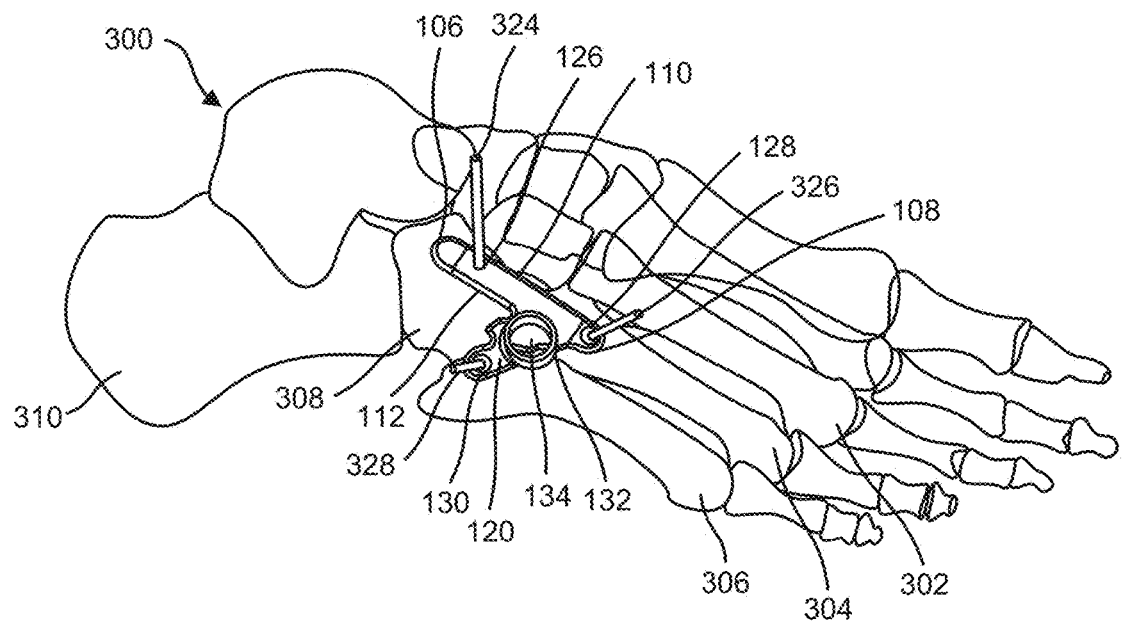
FIG. 26 is a top perspective view of the foot of FIG. 25 after removal of the joint preparation paddle, in accordance with an aspect of the present disclosure.
Figure 27:
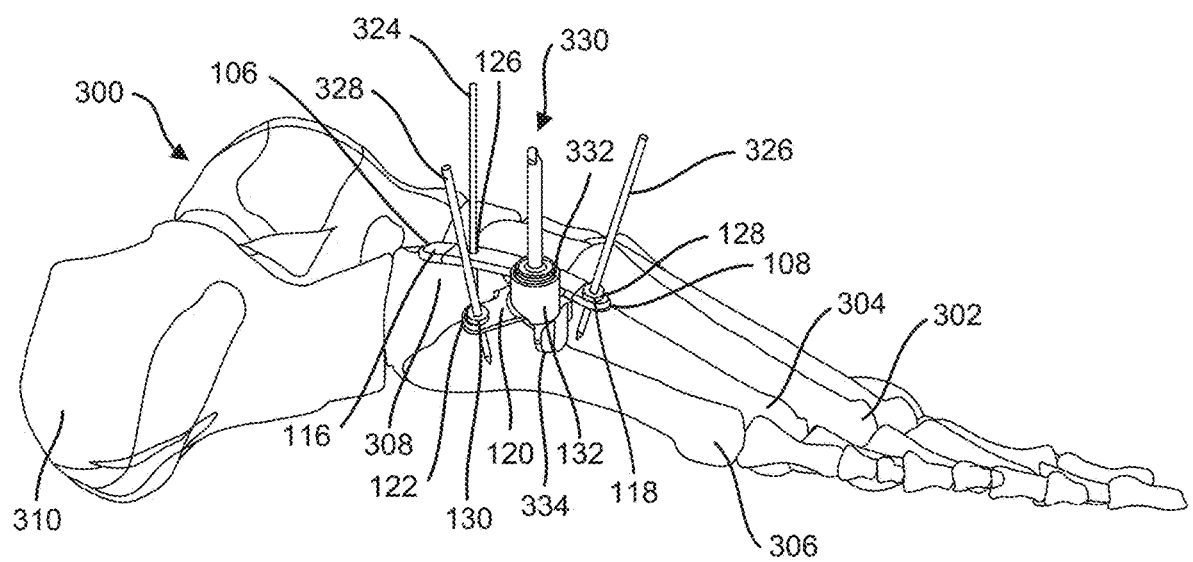
FIG. 27 is a side perspective view of the foot of FIG. 26 with a reamer inserted through the alignment guide and into the foot, in accordance with an aspect of the present disclosure.

After the wires 324, 326, 328 are inserted into the bones 308, 304, 306, respectively, the joint preparation paddle 260 may be removed from the template 100, as shown in FIG. 26. Then, the placement of the template 100 may be confirmed under fluoroscopy. If the template 100 is in the desired position, a reamer 330 may be selected to correspond to the hole 134 in the selected template 100. The reamer 330 may be attached to a handle (not shown) and the reamer 330 may be inserted into the hole 134 in the template 100 until the distal end of the reamer 330 contacts bone. The reamer 330 may include a plurality of solid and dashed lines 332 positioned around the circumference of the head portion of the reamer 330, as shown in FIG. 27. Once the reamer 330 contacts the bones 304, 306, the surgeon should note which solid or dashed line 332 is closest to the top of the reamer guide 132. Next, the bones 304, 306 may be reamed until the next solid or dashed line 332, respectively, of the reamer 330 to ensure adequate depth of the reamed hole 334, as shown in FIGS. 27 and 28. With continued reference to FIG. 28, after the hole 334 is reamed the second and third wires 326, 328 may be removed. In addition, the template 100 may be removed by sliding the template 100 off the first wire 324.

Figure 29:
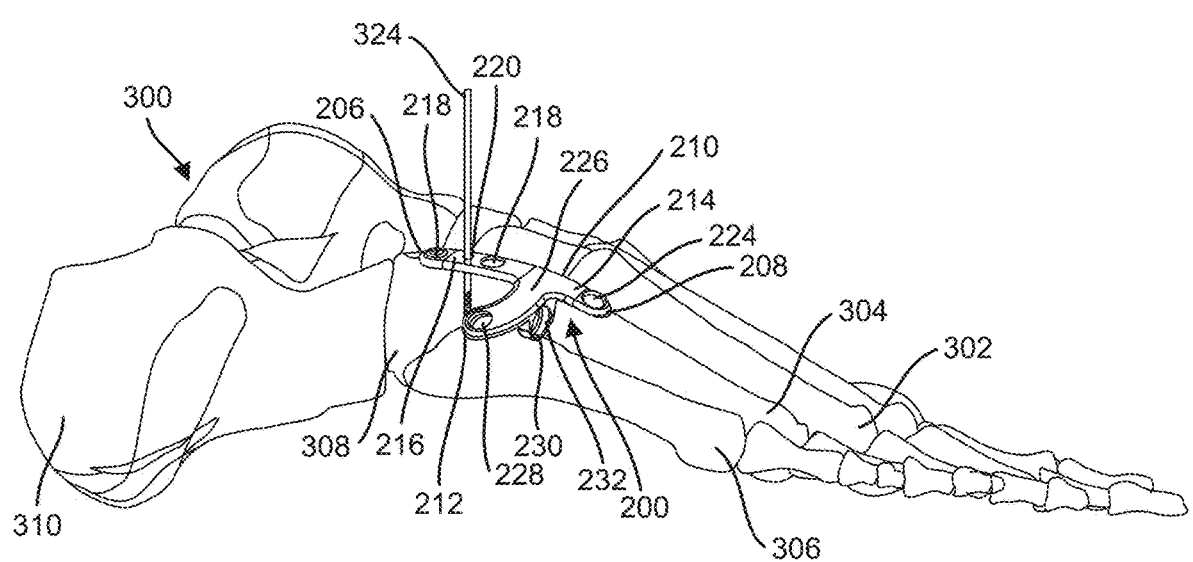
FIG. 29 is a side perspective view of the foot of FIG. 28 after insertion of the implant of FIG. 11, in accordance with an aspect of the present disclosure.
Figure 30:
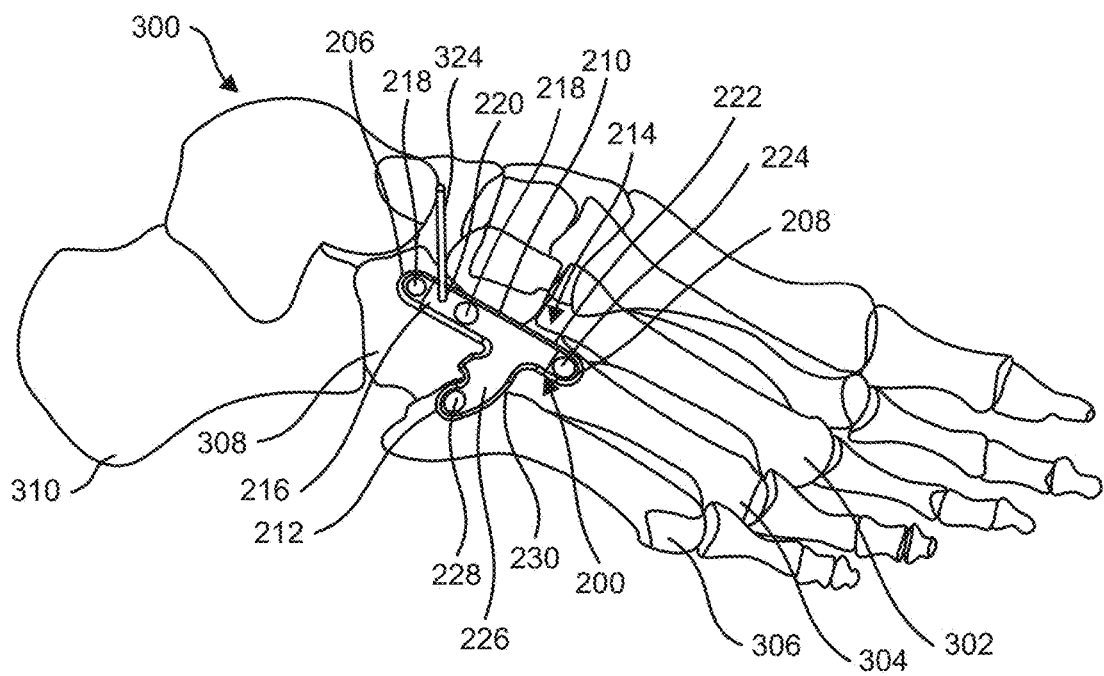
FIG. 30 is a top perspective view of the foot of FIG. 29, in accordance with an aspect of the present disclosure.

Referring now to FIGS. 29 and 30, an implant 200 may be selected and slid over the first wire or proximal k-wire 324. The wire 324 may be inserted into the hole 220 of the implant 200 and the implant 200 may be slid down the wire 324 until the plantar extension member 230 is positioned into the reamed hole 334. Next, the size and position of the implant 200 may be confirmed. In some embodiments, the implant 200 may need to be removed and replaced with a larger or smaller implant. The distance between the extension member 230 of each implant 200 and the hole 220 is constant. The constant distance allows the implant 200 to be replaced with a larger or smaller implant 200 without having to remove or move the first wire 324 to achieve the proper position of the extension member 230 of the larger or smaller implant 200. In other embodiments, if the extension member 230 does not seat properly in the $4^{th}/5^{th}$ metatarsal joint, then the implant 200 may be removed and additional reaming performed by reinserting the template 100 onto the foot 300.

Figure 32:
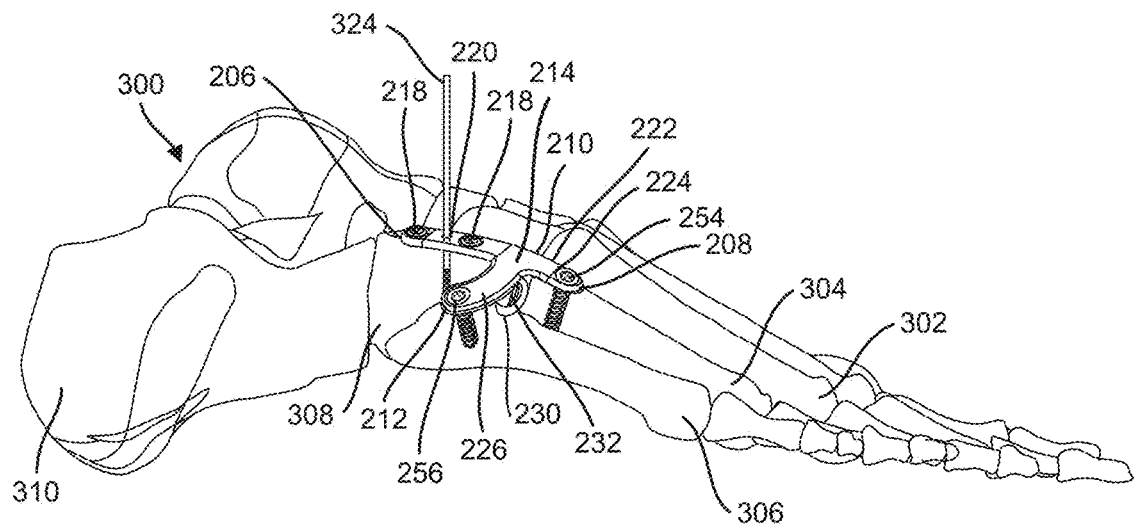
FIG. 32 is a side perspective view of the foot of FIG. 31 after insertion of two bone fasteners through the implant and into the foot, in accordance with an aspect of the present disclosure.

Once the desired size and position of the implant 200 is achieved, a fourth wire 336, for example, a threaded olive wire, may be inserted into the second fastener hole 224 to secure the position of the implant 200, as shown in FIG. 31. In addition, the method may include inserting a drill guide 338 into the third fastener hole 228 of the third arm 226 of the implant 200. Then, a drill bit 340 corresponding to the desired fastener diameter may be inserted into the drill guide 338 and an opening (not shown) in the bone 306 may be drilled. The opening may be drilled to a depth corresponding to the length of the fastener being inserted. The depth may be determined using, for example, a depth gauge (not shown). After the opening (not shown) is drilled, the drill bit 340 and drill guide 338 may be removed from the implant 200 and a third fastener 256 may be inserted through the third fastener hole 228 of the implant 200 and into the fifth metatarsal 306, as shown in FIG. 32. Next, the wire 336 may be removed and the drill guide 338 may be coupled to the second fastener hole 224. An opening (not shown) in the fourth metatarsal 304 may then be drilled as described above with reference to the opening (not shown) drilled into the fifth metatarsal, which will not be described again here for brevity sake. Once the opening (not shown) is drilled in the fourth metatarsal 304, the drill bit 340 and drill guide 338 may be removed from the implant 200 and a second fastener 254 may be inserted through the second fastener hole 224 of the implant 200 and into the fourth metatarsal 304.

Figure 34:
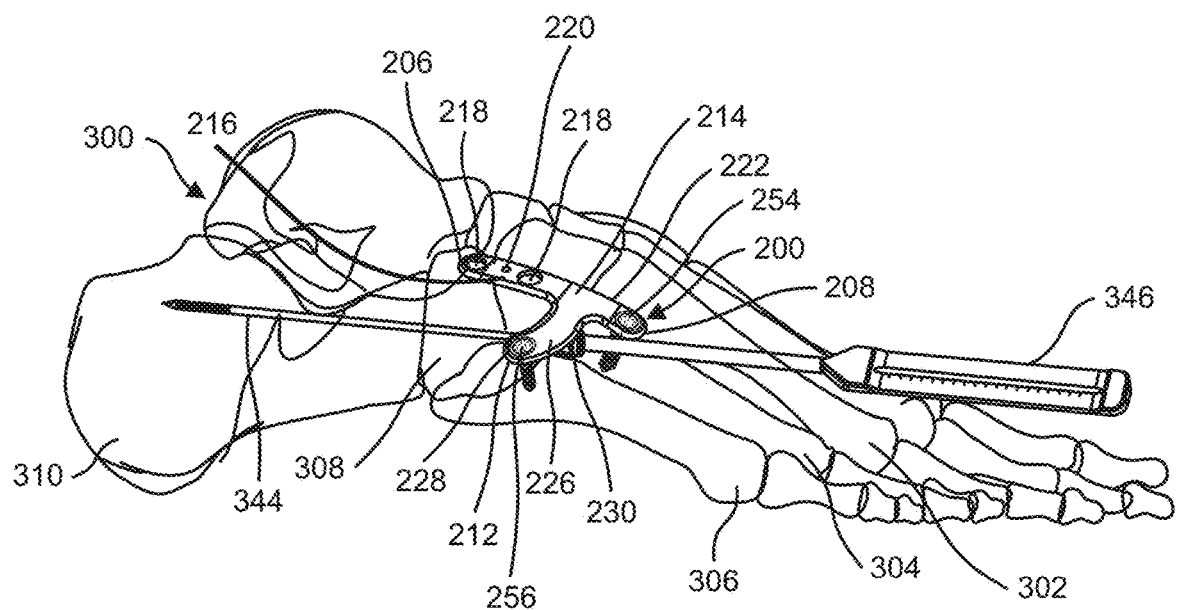
FIG. 34 is a side perspective view of the foot of FIG. 33 after removal of the k-wire guide and insertion of a depth gauge over the k-wire, in accordance with an aspect of the present disclosure.
Figure 35:
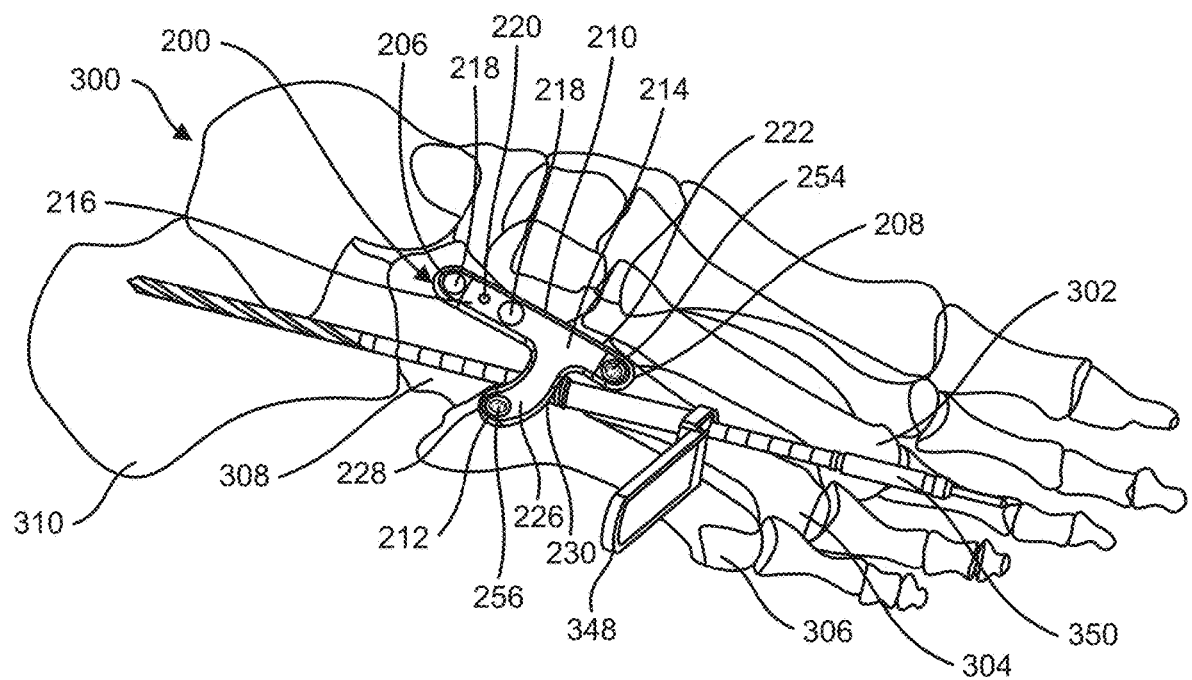
FIG. 35 is a top perspective view of the foot of FIG. 34 after removal of the depth gauge and insertion of a soft tissue protector over the k-wire and a drill bit inserted through the tissue protector and over the k-wire, in accordance with an aspect of the present disclosure.

Referring now to FIG. 33, the first wire 324 may then be removed from the cuboid 308 and a k-wire guide 342 may be secured to the plantar extension member 230. The k-wire guide 342 may be inserted into and coupled to the hole 232 of the extension member 230. A wire 344, for example, a threaded k-wire, may be inserted through the guide 342 and into the central aspect of the calcaneus 310, as shown in FIG. 33. Once the k-wire 344 is inserted into the calcaneus 310, the guide 342 may be removed. A cannulated depth gauge 346 may then be inserted over the wire 344 to measure the length of the wire 344, as shown in FIG. 34. Next, the method may include inserting a soft tissue protector 348 over the wire 344 and coupling the soft tissue protector 348 to the hole 232 of the extension member 230 of the implant 200, as shown in FIG. 35. Then, a drill bit 350 may be inserted over the wire 344 and through the soft tissue protector 348 and hole 232 to drill a path between the fourth and fifth metatarsals 304, 306 and an opening in the cuboid 308 and calcaneus 310. After the path between the fourth and fifth metatarsals 304, 306 and the opening is drilled in the cuboid 308 and calcaneus 310, the drill bit 350, the soft tissue protector 348, and the wire 344 may be removed from the foot 300.

Figure 36:
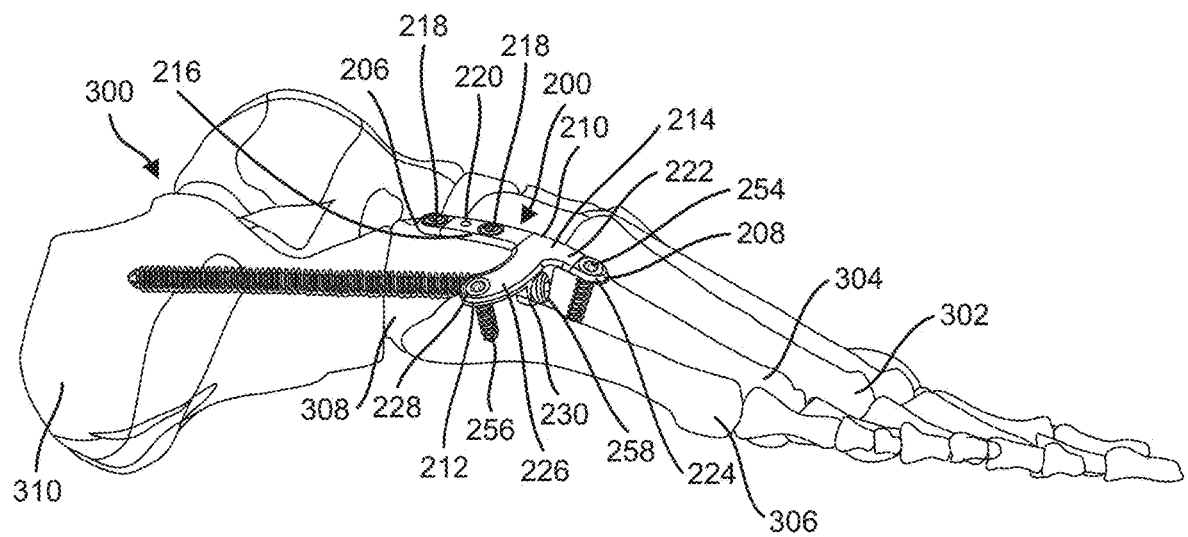
FIG. 36 is a side perspective view of the foot of FIG. 35 after removal of the drill, tissue protector and k-wire and insertion of a beam fastener, in accordance with an aspect of the present disclosure.

A beam fastener 258 may then be inserted into the opening in the cuboid 308 and calcaneus 310 through the hole 232 in the extension member 230 of the implant 200, as shown in FIG. 36. The temporary fixators 312, 314, 316 may be removed during insertion of the fastener 258 or after insertion of the fastener 258. For example, if the fastener 258 is a compression fastener, the temporary fixators 312, 314, 316 may be removed from the joints 318, 320, 322 as the tip of the fastener 258 advances past each joint and creates a compressive force as the fastener 258 is inserted. After the fastener 258 is inserted, the length and position of the fastener 258 may be confirmed using fluoroscopy.

Figure 37:
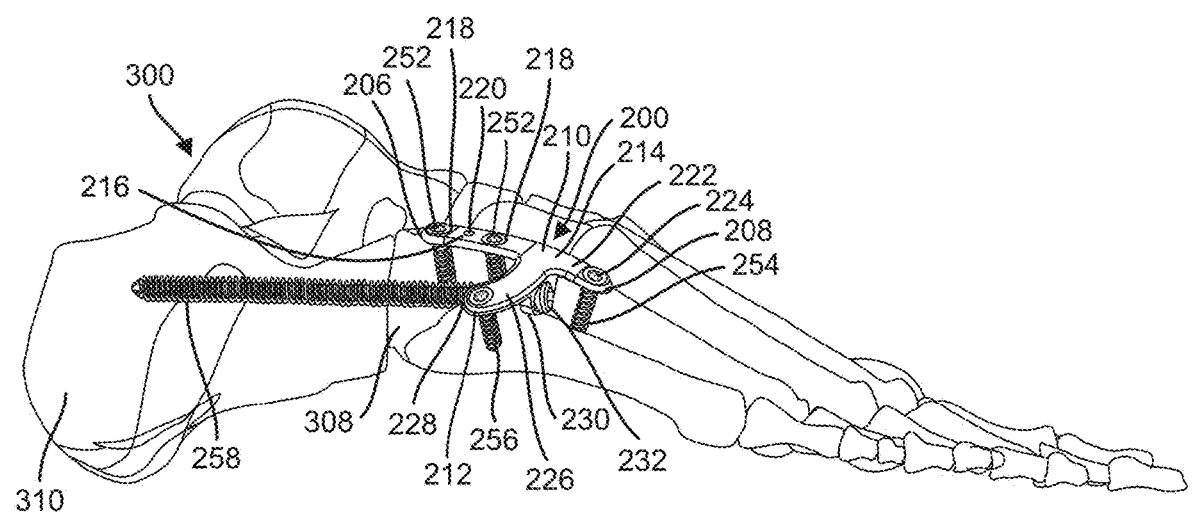
FIG. 37 is a side perspective view of the foot of FIG. 36 after insertion of two additional bone fasteners through the implant and into the foot, in accordance with an aspect of the present disclosure.

Next, the fasteners 252 may be inserted through the first fastener holes 218, as shown in FIG. 37. Although not shown, the fasteners 252 may be inserted as described in greater detail above with reference to FIGS. 31 and 32. The method includes inserting a drill guide 338 into one first fastener hole 218 of the first arm 216 of the implant 200. Then, the drill bit 340 corresponding to the desired fastener diameter may be inserted into the drill guide 338 and a first opening (not shown) in the bone 308 may be drilled. The first opening may be drilled to a depth corresponding to the length of the fastener being inserted. The depth may be determined using, for example, a depth gauge (not shown). After the first opening (not shown) is drilled, the drill bit 340 and drill guide 338 may be removed from the implant 200 and one first fastener 252 may be inserted through the one first fastener hole 218 of the implant 200 and into the cuboid 308, as shown in FIG. 37. A second first fastener 252 may be inserted into a second first fastener hole 218 of the first arm 216 of the implant 200 as described above with reference to the one first fastener 252 and which will not be described again here for brevity sake. After the fasteners 252, 254, 256, 258 are each inserted into the foot 300 through the implant 200, the method may include performing incision closure or concomitant procedures.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The disclosure has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the disclosure be construed as including all such modifications and alterations.

Having thus described the preferred embodiments, the disclosure is now claimed to be:

1. An implant comprising:
   a body portion;
   a first arm having a first length extending away from the body portion in a first direction along a first axis toward a proximal end of the implant;
   a second arm having a second length extending away from the body portion in a second direction along the first axis, wherein the first direction is opposite the second direction and the first and second arms are each symmetrical about the first axis;
   a third arm extending laterally away from the body portion along a second axis orthogonal to the first axis at a position between the first arm and the second arm, wherein the third arm has a third length along the second axis that is its longest dimension, and wherein the third arm is curved towards the proximal end of the implant as the third arm extends away from the body portion such that an end of the third arm points toward the proximal end, and wherein the first length is longer than each of the second and third lengths; and
   an extension member extending away from a bottom surface of the third arm, wherein the extension member comprises a hole extending through the extension member in a direction substantially parallel to the first and second arms, wherein an outer surface of the extension member is rounded, wherein the extension member has a first taper in a dorsal-plantar direction and a second taper in a medial-lateral direction.

2. The implant of claim 1, wherein the implant further comprises:
   at least one first fastener hole extending through the first arm from a top surface to a bottom surface of the implant;
   at least one second fastener hole extending through the second arm from the top surface to the bottom surface of the implant; and
   at least one third fastener hole extending through the third arm from the top surface to the bottom surface of the implant.

3. The implant of claim 1, wherein the implant further comprises:
   a hole extending through the first arm from a top surface to a bottom surface of the implant.

4. The implant of claim 3, wherein the hole of the implant is configured to receive at least one guide wire.

* * * * *